United States Patent [19]

Heldin et al.

[11] Patent Number: 5,227,302
[45] Date of Patent: Jul. 13, 1993

[54] DNA ENCODING PLATELET DERIVED ENDOTHELIAL CELL GROWTH FACTOR (PD-ECGF)

[75] Inventors: Carl-Henrik Heldin, Uppsala, Sweden; Kohei Miyazono, Tokyo, Japan; Christer Wernstedt; Ulf G. T. Hellman, both of Uppsala, Sweden; Fumimaro Takaku; Fuyuki Ishikawa, both of Tokyo, Japan

[73] Assignee: Ludwig Institute for Cancer Research, N.Y.

[21] Appl. No.: 742,092

[22] Filed: Aug. 2, 1991

Related U.S. Application Data

[63] Continuation of Ser. No. 288,056, Dec. 20, 1988, abandoned.

[51] Int. Cl.$^5$ .................. C07H 21/04; C12N 15/00; C12N 15/18; C12N 15/12
[52] U.S. Cl. .................. 435/240.2; 536/23.51; 536/23.5; 435/252.3; 435/252.33; 435/320.1; 530/350; 530/399
[58] Field of Search .................. 530/380, 399; 435/122.3, 320.1, 240.2, 252.3, 252.33, 11, 13; 536/27

[56] References Cited

U.S. PATENT DOCUMENTS 4,868,113  9/1989  Jaye .......................... 435/70
4,920,210  4/1990  Koszalka et al. ............ 536/24

OTHER PUBLICATIONS

Folkman, J., *Cancer Research*, 46, pp. 467–473, 1986.
Miyazono, K. et al., *J. Biol. Chem.*, 262 (9): 4098–4103, 1987.
Ishikawa, F. et al., *Nature*, 338, pp. 557–561, 1989.
Pizonica-Ubrms, H. et al., *Molecular and Cellular Biology*, 6(6): 2033–2039, 1986.
Miyazono et al., Biochem. & Biophys. Res. Comm. 126(1): 83–88 (Jan. 16, 1985).
Miyazono et al., Exp. Cell Res. 159: 487–494 (1985).
Miyazono et al., Biochem. 28: 1704–1710 (1989).
Usuki et al.; Proc. Natl. Acad. Sci. 86: 7427–7431 (Oct. 1989).
Desgranges et al., Biochim. et Biophys. Acta.654: 211–218 (1981).
Walter et al., J. Biol. Chem. 265(23): 14016–14022 (1990).

*Primary Examiner*—Robert J. Hill, Jr.
*Assistant Examiner*—Marianne Porta Allen
*Attorney, Agent, or Firm*—Felfe & Lynch

[57] ABSTRACT

Platelet-derived endothelial cell growth factor (PD-ECGF) is a 45 kDa endothelial cell mitogen that has been purified to homogeneity from human platelets. It does not bind to heparin and does not stimulate the proliferation of fibroblasts, in contrast to other endothelial mitogens of the fibroblast growth factor (FGF) family. PD-ECGF appears to be the only endothelial cell growth factor in human platelets and recent data indicate that it has angiogenic activity in vitro, i.e., the ability to stimulate the formation of new blood vessels and chemotactic activity, in vitro. The present invention provides a homogeneous PD-ECGF in substantially greater yields than available in the past, the primary structure of PD-ECGF, antibodies against PD-ECGF, clones of its cDNA, and variants thereof. The invention also provides a therapeutic preparation of PD-ECGF.

11 Claims, 26 Drawing Sheets

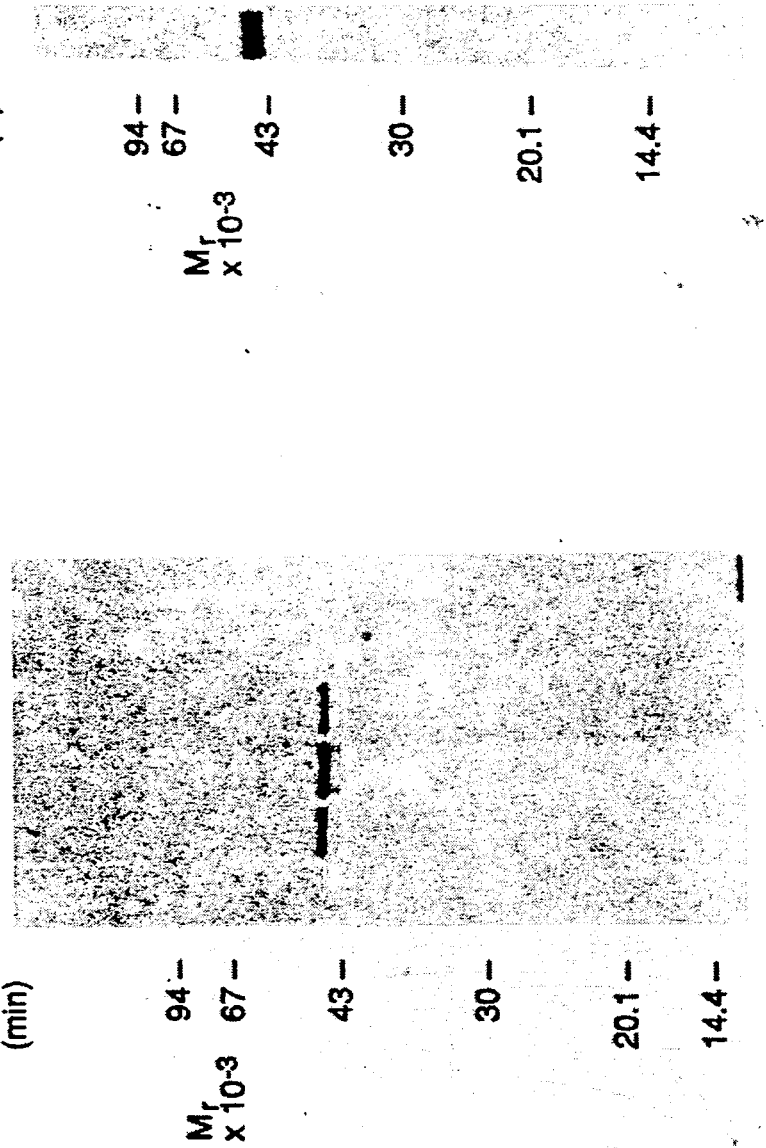

FIG. 9

```
MAALMTPGTGAPPAPGDFSGEGSQGLPDPSPEPKQLPELIRMKRDGGRLSEADIRGFVAA    60
     /--------------/....../......./......
     /+++++++++++++/+++++++++++++
■
VVNGSAQGAQIGAMLMAIRLRGMDLEETSVLTQALAQSGQQLEWPEAWRQQLVDKHSTGG   120
..                          /.............../......
   *  *
VGDKVSLVLAPALAACGCKVPMISGRGLGHTGGTLDKLESIPGFNVIQSPEQMQVLLDQA   180
................/........./......
 * *
GCCIVGQSEQLVPADGILYAARDVTATVDSLPLITASILSKKLVEGLSALVVDVKFGGAA   240
....                              /.............../.....
                                          *
VFPNQEQARELAKTLVGVGASLGLRVAAALTAMDKPLGRCVGHALEVEEALLCMDGAGPP   300
                 /............./.................
DLRDLVTTLGGALLWLSGHAGTQAQGAARVAAALDDGSALGRFERMLAAQGVDPGLARAL   360
...../....../.
++++++                                                  /++++++++
  *
CSGSPAERRQLLPRAREQEELLAPADGTVELVRALPLALVLHELGAGRSRAGEPLRLGVG   420
.........../....../.......                             /....
=================                                         ▲
AELLVDVGQRLRRGTPWLRVVHRDGPALSGPQSRALQEALVLSDRAPFAAPLPFAELVLPPQQ  482
.........../........./......S........
           /+++++++++++++++S+++
```

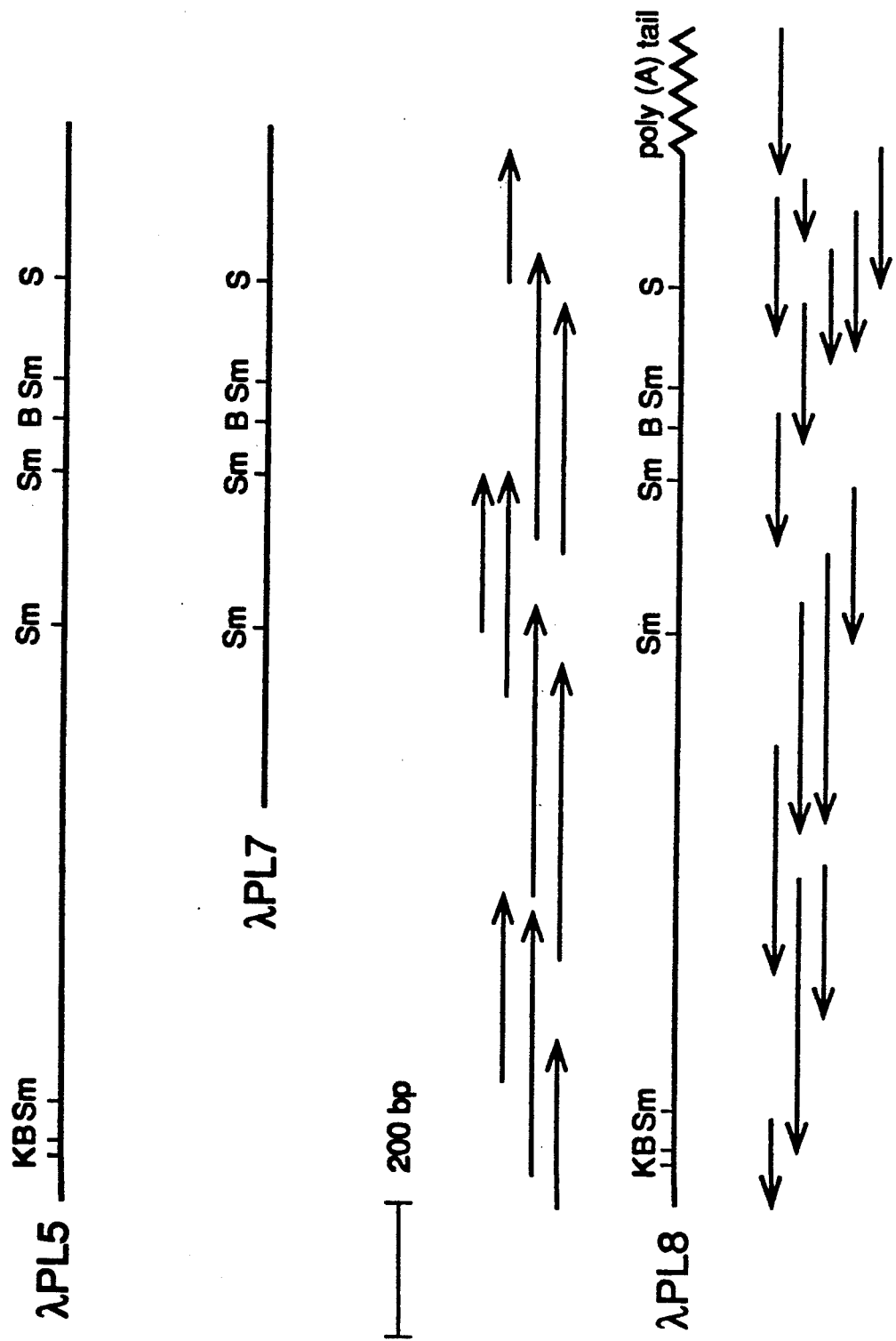

FIG. 11B

```
 1   GGGCAGTGGA   CCGCTGTGCG   CGAACCCTGA   ACCCTACGGT   CCCGACCCGC   GGGCGAGGCC
61   GGGTACCTGG   GCTGGGATCC   GGAGCAAGCG   GGCGAGGGCA   GCGCCCTAAG   CAGGCCCGGA
                                                                258
121  GCG ATG GCA GCC TTG ATG ACC CCG GGA ACC CCG GGA ACC CCA CCC GCG CCT GGT GAC TTC TCC
 1   Met Ala Ala Leu Met Thr Pro Gly Thr Pro Gly Ala Pro Pro Ala Pro Gly Asp Phe Ser

181  GGG GAA GGG AGC CAG GGA CTT CCC GAC CCT TCG CCA GAG CCC AAG CAG CTC CCG GAG CTG
 20  Gly Glu Gly Ser Gln Gly Leu Pro Asp Pro Ser Pro Glu Pro Lys Gln Leu Pro Glu Leu

241  ATC CGC ATG AAG CGA CGA GGA GGC CGC CTG AGC GAA GCG GAC ATC AGG GGC TTC GTG GCC
 40  Ile Arg Met Lys Arg Arg Gly Gly Arg Leu Ser Glu Ala Asp Ile Arg Gly Phe Val Ala

301  GCT GTG GTG AAT GGG AGC GCG CAG ATC GGG GCC ATG CTG ATG GCC ATC CGA
 60  Ala Val Val Asn Gly Ser Ala Gln Ile Gly Ala Met Leu Met Ala Ile Arg

361  CTT CGG GGC ATG GAT CTG GAG ACC TCG GTG CTG ACC CAG GCC CTG CAG TCG GGA
 80  Leu Arg Gly Met Asp Leu Glu Thr Ser Val Leu Thr Gln Ala Leu Gln Ser Gly

421  CAG CAG CTG GAG TGG CCA GAG GCC TGG CGC CAG CAG CTT GTG GAC AAG CAT TCC ACA GGG
100  Gln Gln Leu Glu Trp Pro Glu Ala Trp Arg Gln Gln Leu Val Asp Lys His Ser Thr Gly

481  GGT GTG GAC AAG GTC AGC GTC GTC CTC GCA CCT GCC CTG GCG GCA TGT GGC TGC AAG
120  Gly Val Asp Lys Val Ser Val Leu Val Leu Ala Pro Ala Leu Ala Ala Cys Gly Cys Lys
                              248
541  GTG CCA ATC ATG AGC CGT GGA CGT GGT CTG GGG CAC ACA GGA ACC TTG GAT AAG CTG GAG
140  Val Pro Met Ile Ser Arg Gly Arg Gly Leu Gly His Thr Gly Gly Thr Leu Asp Lys Leu Glu
```

FIG. 11B'

```
601  TCT ATT CCT GGA TTC AAT GTC ATC CAG AGC CAG ATG CAA GTG CTG CTG GAC CAG
160  Ser Ile Pro Gly Phe Asn Val Ile Gln Ser Gln Met Gln Val Leu Leu Asp Gln

661  GCG GGC TGC TGT ATC GTG GGT CAG AGT GAG CAG CTG GTT CCT GCG GAC GGA ATC CTA TAT
180  Ala Gly Cys Cys Ile Val Gly Gln Ser Glu Gln Leu Val Pro Ala Asp Gly Ile Leu Tyr

721  GCA GCC AGA GAT GTG ACA GCC AGC GTG GAC CTC CCA CTC ATC ACA GCC TCC ATT CTC
200  Ala Ala Arg Asp Val Thr Ala Ser Val Asp Leu Pro Leu Ile Thr Ala Ser Ile Leu

781  AGT AAG AAA CTC GTG GAG GGG CTG TCC GCT CTG GTG GAC GTT AAG TTC GGA GGG GCC
220  Ser Lys Lys Leu Val Glu Gly Leu Ser Ala Leu Val Asp Val Lys Phe Gly Gly Ala

841  GCC GTC TTC CCC AAC CAG GAG CAG GCC CGG GAG CTG GCA AAG ACG CTG GTT GGC GGA
240  Ala Val Phe Pro Asn Gln Glu Gln Ala Arg Glu Leu Ala Lys Thr Leu Val Gly Gly
                                                231

901  GCC AGC CTA GGG CTT CGG GTC GCA GCA GCG CTG GAG GAG GCG CTG CTC ATG GAC AAG CCC ATG GAC AAG CCC GGT CGC
260  Ala Ser Leu Gly Leu Arg Val Ala Ala Ala Leu Glu Glu Ala Leu Leu Met Asp Lys Pro Leu Gly Arg

961  TGC GTG GGC CAC GCC GCC CTG GAG GTG GAG GTG GAG GCG CTG CTC TGC ATG GAC AAG CCC GGC GCA GGC CCG
280  Cys Val Gly His Ala Ala Leu Glu Val Glu Ala Leu Leu Cys Met Asp Gly Ala Gly Pro

1021 CCA GAC TTA AGG GAC CTG GTC ACC ACG CTC GGG GGC GCC CTG AGC CTG TGG CTC AGC GGA CAC
300  Pro Asp Leu Arg Asp Leu Val Thr Thr Leu Gly Gly Ala Leu Ser Leu Trp Leu Ser Gly His

1081 GCG GGG ACT CAG GCC CAG GGC GCT GCC CGG GTG GCC GGG GCG CTG GAC GAC GGC TCG GCC
320  Ala Gly Thr Gln Ala Gln Gly Ala Ala Arg Val Ala Ala Ala Leu Asp Asp Gly Ser Ala

1141 CTT GGC CGC TTC GAG CGG ATG CTG GCG GCG CAG GGC GTG GAT CCC GGT CTG GCC CGA GCC
340  Leu Gly Arg Phe Glu Arg Met Leu Ala Ala Gln Gly Val Asp Pro Gly Leu Ala Arg Ala
                             259
```

FIG. 11B"

FIG. 14A
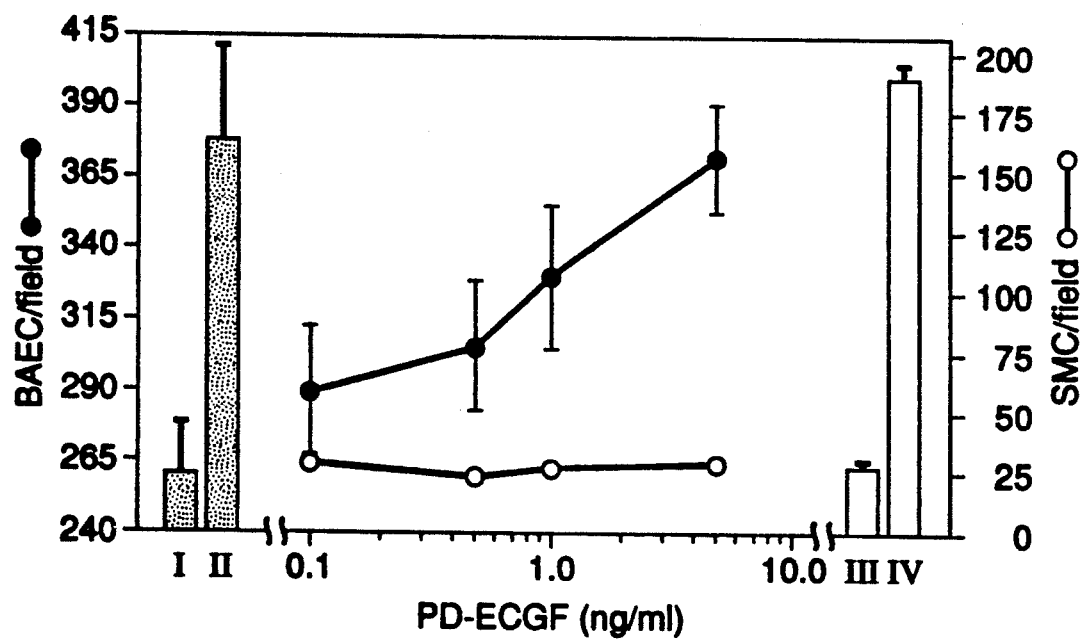
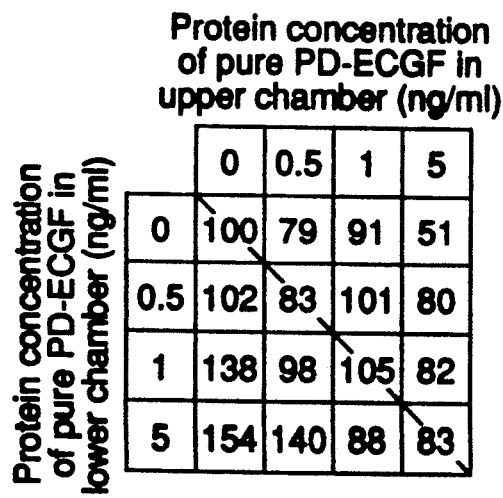
FIG. 14B
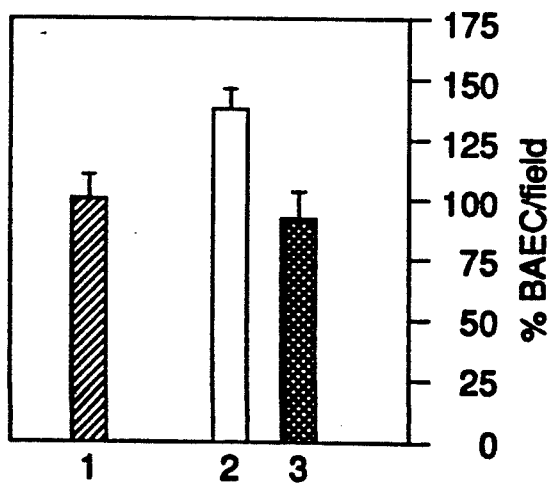
FIG. 14C

DNA ENCODING PLATELET DERIVED ENDOTHELIAL CELL GROWTH FACTOR (PD-ECGF)

This application is a continuation of application Ser. No. 288,056, filed Dec. 20, 1988, now abandoned.

FIELD OF THE INVENTION

Platelet-derived endothelial cell growth factor (PD-ECGF) is a 45 kDa endothelial cell mitogen that has been purified to homogeneity from human platelets. It does not bind to heparin and does not stimulate the proliferation of fibroblasts, in contrast to other endothelial mitogens of the fibroblast growth factor (FGF) family. PD-ECGF appears to be the only endothelial cell growth factor in human platelets and recent data indicate that it has angiogenic activity in vitro, i.e., the ability to stimulate the formation of new blood vessels and chemotactic activity, in vitro. The present invention provides a homogeneous PD-ECGF in substantially greater yields than available in the past, the primary structure of PD-ECGF, antibodies against PD-ECGF, clones of its cDNA, and variants thereof. The invention also provides a therapeutic preparation of PD-ECGF.

BACKGROUND OF THE INVENTION

Polypeptide growth factors play an important role in stimulating proliferation of target cells which are involved in both normal cellular processes and disease states. Some examples of processes that involve cell prolifration are, for instance, epidermal tissue replacement and immune system responses. Hemostasis, which is prevention of blood loss, is a continual process requiring that vascular tissue be constantly replaced. Growth of vascular endothelial cells has a central role in a variety of physiological and pathologicalprocesses, such as angiogenesis, woundhealing, atherosclerosis, and tumor growth. In the case of vascular trauma, a complex series of events comes into operation to maintain hemostasis. Initial response to trauma include activation of platelet plugging, blood coagulation, and eventually regrowth or repair of the damaged tissue. This final step must be activated at the proper time, place and in the proper tissue. One role for polypeptide growth factors is to mediate this response in both a temporal and tissue specific manner.

Peptide and polypeptide growth factors have been isolated from many sources. These include epidermal tissue, neutral tissue, platelets, placental tissue, and others. These peptide and protein factors are distinguished by a variety of properties including target cell specificity, heparin affinity or interaction, secretory properties, and physiochemical properties such as molecular weight, charge, heat stability, pH sensitivity, and susceptibility to reducing agents.

Endothelial cell growth is stimulated by a class of polypeptide growth factors known as fibroblast growth factors (FGFs). These mitogenic factors are characterized by their heparin-binding properties. Heparin is a powerful anticoagulant agent normally found in minute amounts in the circulatory system. The FGFs fall into two distinct protein classes, acidic and basic, and have been identified in neural and other tissues Baird et al., Recent Prog. Horm. Res. 42: 143-205 (1986); Lobb et al., Anal. Biochem. 154: 1-14 (1986); Thomas et al., Trends Biochem. Sci. 11: 81-84 (1986).

Recently, endothelial cell proliferation was shown to be stimulated by a novel polypeptide growth factor that was distinct from other known polypeptide growth factors derived from fresh human platelets Miyazono et al., Biochem. Biophys. Res. Commun. 126: 83-88 (1985); Miyazono et al., Exp. Cell Res. 159: 487-494 (1985). This factor was originally called vascular endothelial cell proliferation factor and was later renamed platelet-derived endothelial cell growth factor PD-ECGF.

Platelets are a rich source of growth factors for a variety of hemopoietic and other tissues. Platelet-derived growth factors that have been identified and characterized include platelet-derived growth factor (PDGF) which stimulates fibroblast and vascular smooth muscle cell growth but has no effect on endothelial cells; transforming growth factor-$\alpha$ (TGF-$\alpha$) which is closely related to epidermal growth factor (EGF) and can stimulate growth of epidermal cells but not endothelial cells; transforming growth factor-$\beta$ (TGF-$\beta$) which synergistically stimulates fibroblast growth in the presence of EGF and is furthermore a potent inhibitor of endothelial cell growth; a hepatocyte growth factor; and platelet-derived endothelial cell growth factor (PD-ECGF), the subject of this invention.

A growth-promoting activity was partially purified and characterized by Miyazono et al. J. Biol. Chem. 262(9): 4098-4103. The following characteristics were used to distinguish this activity from that of previously identified growth factors: Cultured porcine vascular endothelial cells were stimulated to incorporate $^3$H thymidine into DNA in a dose-dependent manner upon treatment with a soluble lysate of fresh human platelets. The platelet lysate also promoted cellular proliferation by about 100% above a control culture treated with 1% fetal bovine serum. Fractionation of the lysate revealed that the activity appeared in the Mr 20,000 range on a Sephadex G-75 gel filtration column, stimulated $^3$H thymidine incorporation into DNA of porcine vascular endothelial cells but not NRK fibroblasts, was probably distinct from PDGF which ran at Mr 30,000 on this column and stimulated fibroblasts but not endothelial cells, was more potent when prepared from fresh platelets rather than from outdated platelets, was heat-and acid-labile, resistant to the reducing agent dithiothreitol and was sensitive to trypsin, guanidinium-HCl and urea, the latter two being denaturants. Based on these characteristics it was concluded that the growth-promoting activity was a polypeptide growth factor distinct from any that had previously been identified in human platelets.

Angiogenesis is the formation of new capillary blood vessels by sprouting from existing vessels. It is an important process in wound healing and tumor growth. Certain polypeptide factors have been identified which stimulate this process by virtue of their mitogenic or chemotactic activity for andothelial cells.

Mitogens are substances that stimulate proliferation of cells and are usually small molecules such as phorbal esters, polysaccharides, peptides, proteins or combinations thereof. Taxis is the directed migration of cells in response to an environmental cue. Chemotaxis is thus a response to chemicals in the environment. For eukaryotic cells, known chemotactic factors include histamine, amino acids, peptides, and proteins, Polypeptide factors that elicit angiogenic responses include FGFs, TGF-$\alpha$, TGF-$\beta$, tumor neurosis factor and angiogenin (Folkman et al., Science 235: 442-447 (1987); Frater-Schroeder et al., Proc. Natl. Acad. Sci. USA 84: 5227-5281 (1987); Leibovich et al., Nature 329: 630-632 (1987)). These factors exhibit multiple effects on a wide variety of cell types. Unlike these factors, human platelet-derived endothelial cell growth factor specifically stimulates endothelial cells.

Endothelial cell proliferation inside larger blood vessels is important for the regeneration of damaged endothelium and probably plays a role in prevention of atherosclerosis. Atherosclerosis is a condition in which lipid-rich lesions or plaques develop on blood vessels and can lead to numerous vascuous diseases. Alteration in the endothelial cell layer is thought to be an early event in atherosclerosis. Platelets adhere to damaged endothelium cells and release mitogens to stimulate both endothelial and smooth muscle cell regeneration. PD-ECGF is among the mitogens that are released.

In disease associated with a reduction in platelet number, for example thrombocytopenia, PD-ECGF and other platelet mitogens and chemotactic factors may provide therapeutic benefit. Certain drugs can also induce platelet destruction or suppression. Thus, supplementing drug therapy with platelet mitogens may prevent untoward side effects.

The present source of PD-ECGF is fresh human platelets making purification of large amounts of this protein expensive and potentially risky given that human blood may contain infectious agents. Since PD-ECGF is heat labile, prior sterilization or pasteurization of blood will destroy its activity. To obtain quantities of PD-ECGF for further study and to provide therapeutic amounts, a more readily available source is desired. Cloning the PD-ECGF gene would allow the construction of expression vectors that produce large amounts of PD-ECGF.

The techniques of recombinant DNA technology are well established. While numerous manuals are available that outline the strategy and methodology for cloning genes, much of the work remains unpredictable; there is still no guarantee of success. Each cloning experiment can present its own special problems and pitfalls. A typical strategy for cloning eukaryotic genes is to isolate mRNA, to transcribe it into cDNA which is then inserted into a replicable vector, to transform a suitable host with the construct and to identify the desired clone by any number of means including functional activity or complementation, and screening with antibodies or oligonucleotides. A problem peculiar to some eukaryotic genes is finding a tissue in a state of development or differentiation that is expressing the desired gene product, that is, containing the mRNA from the desired gene. The source of PD-ECGF is platelets which are enucleated cells and thus do not contain DNA or mRNA. Hence, to clone the gene for PD-ECGF a tissue or cultured cell line that produces PD-ECGF was needed to be found.

SUMMARY OF THE INVENTION

The present invention comprises homogeneous platelet-derived endothelial cell growth factor and an improved method for its purification to homogeneity from fresh human platelets. PD-ECGF is a 45 kDal endothelial cell mitogen that does not bind heparin and does not stimulate the proliferation of fibroblasts, in contrast to another class of endothelial cell mitogens which belong to the FGF family. PD-ECGF has angiogenic and chemotactic activity. With greater yields of PD-ECGF available, a partial amino acid sequence can be obtained from tryptic fragments as well as from V8-protease- and CNBr-derived fragments. The present invention provides proteolytic fragments of PD-ECGF and their use in obtaining the amino acid sequence of PD-ECGF and its variants. The PD-ECGF of the present invention provides variants of PD-ECGF.

One embodiment of the invention is to provide oligonucleotides having a DNA sequence deduced from the amino acid sequence of PD-ECGF and their use to identify a cDNA clone of PD-ECGF.

Another object of this invention is to provide polyclonal and monoclonal antibodies against human PD-ECGF and the use thereof in detecting PD-ECGF in mammalian tissues and cells. The antibodies are also used to identify a source of tissue of cells expressing PD-ECGF that can provide mRNA to make cDNA and thus permit cloning of the gene for PD-ECGF.

A further embodiment of the present invention provides a nucleic acid molecule encoding the amino acid sequence of platelet-derived endothelial cell growth factor from mammalian platelets of placenta especially human.

Yet another embodiment is the expression of PD-ECGF by a replicable expression vector containing the gene encoding for PD-ECGF.

Still another embodiment is the use of PD-ECGF as a therapeutic agent for treatment of atherosclerosis, wound healing and to induce angiogenesis and specific chemotaxis of endothelial cells.

BRIEF DESCRIPTION OF THE DRAWINGS

FIG. 7A-C. Chromatographic purification of human PD-ECGF on an alkyl Superose column. A) Column profile. B) Analysis of fractions by SDS gel electrophoresis and silver staining.

FIG. 9. The amino acid sequence of human PD-ECGF obtained by sequencing proteolytic fragments of PD-ECGF.

FIG. 11 A). Restriction may and sequencing strategy of human placental DNA coding for PD-ECGF. B,B',B") Nucleotide sequence of human PD-ECGF DNA.

FIG. 14 A). Dose dependent effect of PD-ECGF on migration of bovine aortic endothelial cells (BAECs) B) Checkerboard data showing chemotaxics of BAECs C) Neutralization of chemotaxis by antibodies to PD-ECGF.

DETAILED DESCRIPTION OF THE INVENTION

Figure 1:
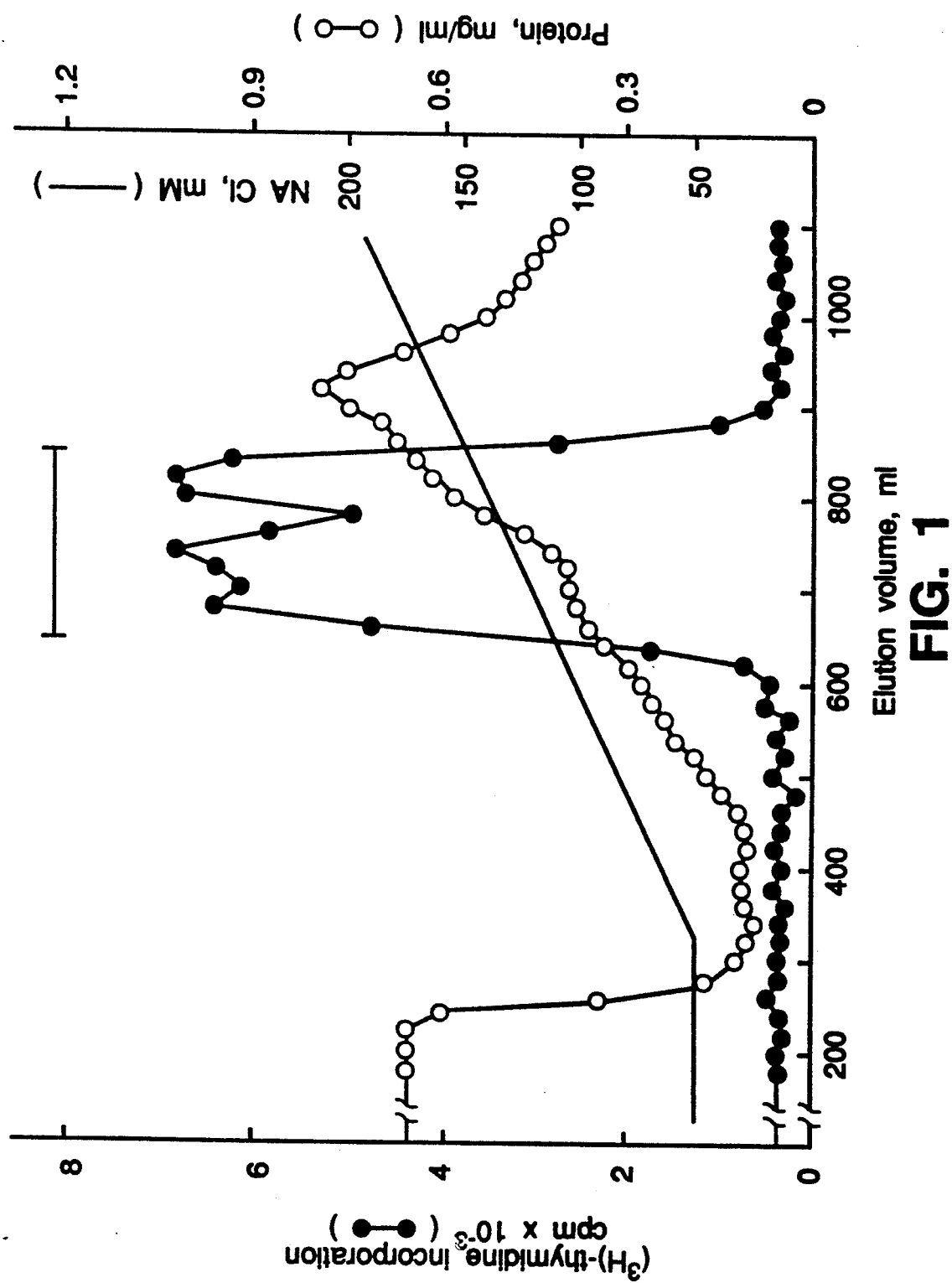
FIG. 1. Chromatographic purification of human PD-ECGF on DEAE-Sepharose.

Vascular endothelial cells make a functional monolayer between blood and underlying tissue. In a normal vessel wall, endothelial cells are known to exist in a quiescent growth state. Proliferation of endothelial cells is a key component to a number of biological processes such as wound repair, thrombosis, atheroscelorsis and tumor growth. Thus, factors that regulate endothelial cell proliferation play a key role in these conditions.

Factors with the ability to stimulate the formation of blood vessels are implicated as causative agents in angiogenesis of normal a malignant tissue, and this is reviewed by Wolkman et al. The most well-characterized factors in this category are FGFs, which are a family of heparin-binding endothelial cell mitogens originally isolated from neural tissue but are also found in macrophages and other tissues. Another endothelial cell mitogen is PD-ECGF.

PD-ECGF growth-promoting activity can be assayed by determining the incorporation of $^3$H-thymidine into the DNA of endothelial cells. Cells typically used in the assay are porcine aortic endothelial cells with bovine aortic endothelial cells, and human umbilical endothelial cells also being stimulated by PD-ECGF. Other established, cultured endothelial cell lines can be used in the assay with porcine aortic cells being preferred for routine assays.

Growth-promoting activity of PD-ECGF is also assayed by measuring cell proliferation. In this assay, fresh cells are plated in culture and the actual number of cells present is determined and compared to a control that has not received PD-ECGF. The cultured cell lines sutable for this assay are the sane as described in the $^3$H-thymine incorporation assay.

When assayed on FGF cultures PD-ECGF does not stimulate incorporation of $^3$H thymidine into DNA nor does it induce cell proliferation.

PD-ECGF from platelets, especially human platelets, has been purified in small quantities (Miyazono et al., J. Biol. Chem. 262: 4098–4103 (1987). It has thus far been characterized as a 45 kDal polypeptide that is heat and acid labile, resistant to reducing agents such as dithiothreitol and others, and sensitive to proteolytic degradation, especially by trypsin and other serine proteases, and any of a number of well characterized proteases. The availability of larger amounts of pure PD-ECGF allows at least a partial amino acid sequence to be obtained in order to facilitate the cloning of its gene.

The purification of PD-ECGF is complicated by the fact that PD-ECGF occurs in low quantities in platelets and that its biological activity is both heat and acid labile. The process described by Miyazono et al. supra is a seven step process using both conventional chromatography and Fast Performance Liquid Chromatography (FPLC). The present invention contemplates an improved purification procedure that results in higher purity and substantially greater yields of PD-ECGF.

The present purification process begins with a side fraction of a platelet lysate in the purification of PDGF. This fraction is obtained by cation exchange chromatography on CM-Sephadex. The first step is anion exchange chromatography in batch on QAE-Sephadex. Next, the pooled fractions are concentrated by ammonium sulfate precipitation at about 42% of saturation. The third step is also anion exchange chromatography but on DEAE-Sepharose. The next three steps are all chromatographic involving adsorption chromatography on hydroxylapatite, anion exhange chromatography on Mono Q column attached to an FPLC system (Pharmacia), and gel filtration on a TSK-G4000 SW column. The final step is hydrophobic interaction chromatography on a Superose 12 column.

The present invention is directed to a more rapid process having fewer steps for purification of PD-ECGF that results in about 1,250,000-fold purification at a yield of about 14%, preferably in five steps.

The process is the same as above up to and including the DEAE-Sepharose anion exchange chromatography. Other variations of the purification are also possible even up to this stage. For instance, the platelet lysate can be freshly prepared and need not be a side fraction in the purification of another factor such as PDGF. The chrmoatographic resins employed as described above are preferable for the purification process but other equivalent resins that are commercially available can be substituted with comparable results. Ammonium sulfate precipitation is also done at about 42% saturation; however, one skilled in the art can easily adjust this amount as necessary to precipitate the maximum amount of PD-ECGF activity.

The improvement in the purification process is a reduction in the number of steps following DEAE-Sepharose anion exchange chromatography and speeding the process by using more rapid chromatographic separation techniques that are provided by HPLC, FLPLC and the like. The present process provides homogeneous ECGF in higher yields and evidencing higher biological activity than previously available.

Specifically, the fractions obtained from the DEAE-Sepharose step are pooled and subjected to high performance affinity chromatography on an hydroxylapatite column. This is followed by a final purification step using high peformance hydrophobic interaction chromatography. The resin preferred for this step is alkyl-Superose but other hydrophobic resin are suitable. Such resins are also commercially available. One of ordinary skill in the art can readily determine other suitable resins.

In another aspect of the present invention, antibodies are raised to PD-ECGF. Antibodies are useful in identifying a source of tissues or cells that are expressing PD-ECGF, since platelets are enucleate cells, and therefore, do not contain DNA for expression of the protein. The antibodies can be polyclonal or monoclonal either of which can be prepared by well known methods.

The antibodies of the present invention are raised against homogeneous endothelial cell growth factor, homogeneous PD-ECGF or recombinant PD-ECGF.

The source of endothelial cell growth factor or PD-ECGF may be from mammals or humans and is purified to a level of homogeneity appropriate for raising antibodies. Polyclonal antibodies are prepared in rabbits, goats, sheep and rodents by injecting pure or partially purified PD-ECGF into the animal. After a prescribed series of injections, serum is obtained from the animal and tested for the presence of the desired antibody. The means of identifying a polyclonal antibody against PD-ECGF include immunoblotting, ELISA, Ouchterlony diffusion assay, radioimmuneassay, and other methods well known in the art. In the case of immunoblotting, pure PD-ECGF is run on an SDS acrylamide gel and then transferred to nitrocellolose by electrophoretic transfer in an appropriate buffer. After residual protein binding sites are blocked by any number of blocking agents including bovine serum albumin, Tween-20, non-fat dry milk, and gelatin or other blocking agents, the blot is treated with the antiserum to be tested. This is followed by detection of the bound antibody by a detection means such as $^{125}$I-Protein A with autoradiography or enzyme conjugated second antibodies which give a visible color or fluorescence upon treatment with their substrate.

Monoclonal antibodies against PD-ECGF are prepared by well-known methods. An outline of one method is to inject pure (or partially pure) PD-ECGF into a mouse, to remove its spleen after a response to the antigen has been mounted, to fuse the antibody-producing spleen cells to a myeloma line and to test the resulting hybridomas for production of an antibody that reacts with PD-ECGF by screening the hybridoma culture fluid. One method of screening is to use immunoblotting as described above. Alternatively, screening can be done by dot blotting or by immunofluorescence of a tissue or cell line that contains PD-ECGF.

The present invention provides a nucleic acid encoding the gene for endothelial cell growth factor. The nucleic acid may be a DNA or an RNA molecule, especially preferred is a complementary DNA molecule (cDNA). The cDNA molecule contains the nucleotide sequence encoding a mammalian or human endothelial cell growth factor. Alternatively, the cDNA contains the nucleotide sequence encoding mammalian or human DP-ECGF. The nucleotide sequence can be from PD-ECGF, derived from the amino acid from human placenta, sequence of human platelet. PD-ECGF which differs from the placental source by ten amino acids and a single residue change of a leucine to a serine at Position 471.

The cloning of the PD-ECGF gene requires indentifying a source of mRNA from a cell line or tissue that expresses PD-ECGF because the major source of PD-ECGF in platelets which are cells that lack nuclei. Several hematopoetic cell lines were tested for the presence of PD-ECGF using either a polyclonal or monoclonal antibody and immunoblotting of extracts of these tissues. It might be expected that hemotopoetic cells would also produce PD-ECGF, since they are related to platelets; however, none of the lines examined produced PD-ECGF. Human placental tissue was tested in the same manner and found to express PD-ECGF. Polyclonal antibodies would be expected to cross react with PD-ECGF from other mammalian sources. Thus, other tissues from humans and mammals can be readily tested by these methods to determine if they express PD-ECGF and provide sources of mRNA for cloning the PD-ECGF gene.

Purified poly (A)+mRNA is isolated by procedures that are well known. The method of Han et al., J. Biochem. 261 1617–1625 (1987), is one such method but others can be found in standard laboratory manuals on recombinant DNA technology.

The selected mRNA is transcribed into a cDNA molecule using reverse transcriptase to make the primary strand, oligo (dG) tailing with terminal transferase and completing the double stranded molecule by priming with oligo (dC) primers. Other methods of preparing cDNAs for cloning can also be found in standard laboratory manuals on recombinant DNA technology.

The cDNA is inserted into a replicable vector which may include bacteriophage derivatives. Especially preferred are lambda phage vectors which include but are not limited to λgt10 and λgt11.

The desired clone can be detected by a number of techniques. Antibodies can be used when a replicable expression vector such asλgt11 is used for the cloning. Radiolabelled oligonucleotides are useful in identifying a desired gene. The sequence for the oligonucleotide is deduced from the amino acid sequence of the PD-ECGF by the method of Lathe J. Molec. Biol. 183: 1–12 (1985) or by inspection of the genetic code for the given amino acid seuqence. Preferrably a region of amino acid sequence is selected that maximizes the use of unique codons. Oligonucleotides can be synthesized by well-known methods on automated DNA synthesizers and can be any length from about 15 to about 100 nucleotides. The sequence of the oligonucleotide probes of the present invention are listed in the examples. Hybridization of the probes to clones carrying potential inserts is also well established and methods therefor can be found in standard laboratory manuals on recombinant DNA technology.

Clones that carry the PD-ECGF gene are sequenced by dideoxy chain termination by the method of Sanger or by the chemical method of Maxam and Gilbert.

The cDNA clones of PD-ECGF are useful for identifying homologous genes in mammals, determining the genomic-organization of the PD-ECGF gene in mammals, identifying PD-ECGF gene transcripts, cloning the genomic gene, especially human, and in constructing expression vectors to produce recombinant PD-ECGF from mammals, especially humans. Identifying homologous genes and determining the structure of the genomic gene are done by Southern hybridization of total genomic DNA. Cellular mRNA is analyzed by Northern blotting. Both Southern blotting and Northern blotting techniques are widely practiced and the methodology therefor is available in standard laboratory manuals on recombinant DNA technology. To clone the genomic PD-ECGF gene, the technology described in this invention is used except that the source of DNA is genomic DNA, and the hybridization probe is the cDNA clone rather than the oligonucleotides.

The deduced amino acid sequence of human placental PD-ECGF differs from human platelet PD-ECGF by one amino acid at position 471 where a leucine residue replaces a serine residue identified by direct amino acid sequencing. It also contained ten additional amino acids at the amino terminus of the protein. It is unknown if this difference is the result of a processing event. Other variants of PD-ECGF may be cloned from other tissue sources such as bovine or porcine placental tissue and other tissues. These varients are useful for replacing humabn PD-ECGF in therapeutic uses that are described below.

Such vectors contain one or more selectable markers for maintainence of the plasmid and DNA sequence elements that are operably linked to a gene to control expression of that gene. These DNA sequence elements include promotors, enhancer elements, transcription termination signals and polyadenylation sites. The latter three are not always necessary and will depend on the replicable expression vector and the host system that is used to obtain expression. Promotors are DNA sequence elements that control gene expression. Prokaryotic promotors that are useful include the lac promotor, the trp promotor, the $P_L$ and $P_R$ promotors of lambda and the T7 polymerase promotor. Eukaryotic promotors are also useful in the invention and include promotors of viral origin and yeast promotors, especially the Molone Leukemia Virus LTR.

Expression of PD-ECGF is obtained by subcloning its gene into a replicable expression vector. Replicable expression vectors that are suitable for expression of PD-ECGF include bacterial and bacteriophage vectors that can transform such hosts as E. coli, B. subtilis and other microorganisms. Many of these vectors are based on pBR322 including Bluescript (commercially available from Stratagene) and are well known in the art. Bacteriophage vectors that are used in the invention include lambda and M13.

Other suitable vectors for PD-ECGF expression are derived from eukaryotic sources. Expression vectors that function in yeast and cell culture are used to express PD-ECGF. These vectors include yeast plasmids, retrovirus vectors, BPV vectors, baculovirus vectors, and other viral vectors. Tissue culture cells that are used with eukaryotic replicable expression vectors include NIH3T3 cells, mouse L cells, COS-7 cells, HeLa cells and other established cultured cell lines, NIH 3T3 cells are preferred.

The replicable expression vectors of this invention are made by subcloning the cDNA insert from PL8 into the desired vector. In this invention, one replicable expression vector is plasmid pLJ, which contains the Molone leukemia virus LTR to drive the cDNA transcription and a neomycin resistance gene as a selection marker. When the cDNA for PD-ECGF is subcloned into this vector, the plasmid pLPL8J is made. This vector is transformed to NIH3T3 cells by the calcium phosphate co-precipitation method. Analysis of a cell lysate and conditional medium of one cell transformed with pLPL85 revealed growth promoting activity for procine aortic endothelial cells in the cell lysate but not in the conditioned medium. The activity is inhibited by PD-ECGF antibodies and upon immunoblotting with PD-ECGF antibodies reveals the presence of a recombinant PD-ECGF protein of 45 kDal.

Other replicable expression vectors are constructed and tested in a similar manner. One skilled in the art has available many choices of replicable expression vectors, compatible hosts and well known methods for making and using the vectors.

Transformant microorgansims and cultured cells are made by introducing a replicable expression vector into the system by transformation. Processes for transformation are well known in the art and include $CaCl_2$ treatment and electroporation of bacterial cells, calcium phosphate co-precipitation, protoplast fusion and electroporation for eukaryotic cells. The detailed methods for these techniques can be found in standard laboratory manuals on recombinant DNA technology.

Homogeneous PD-ECGF was sequenced at the protein level and has the sequence:

```
                                M A A L M T P G T G A P P A P G D F S

G E G S Q G L P D P S P E P K Q L P E L I R M K R D G G R L

S E A D I R G F V A A V V N G S S Q G A Q I G A M L M A I R

L R G M D L E E T S V L T Q A L A Q S G Q Q L E W P E A W R

Q Q L V D K H S T G G V G D K V S L V L A P A L A A C G C K

V P M I S G R G L G H T G G T L D K L E S I P G F N V I Q S

P E Q M Q V L L D Q A G C C I V G Q S E Q L V P A D G I L Y

A A R D V T A T V D S L P L I T A S I L S K K L V E G L S A

L V V D V K F G G A A V F P N Q E Q A R E L A K T L V G V G

A S L G L R V A A A L T A M D K P L G R C V G H A L E V E E

A L L C M D G A G P P D L R D L V T T L G G A L L W L S G H

A G T Q A Q G A A R V A A A L D D G S A L G R F E R M L A A

Q G V D P G L A R A L C S G S P A E R R Q L L P R A R E Q E

E L L A P A D G T V E L V R A L P L A L V L H E L G A G R S
```

R A G E P L R L G V G A E L L V D V G Q R L R R G T P W L R

V H R D G P A L S G P Q S R A L Q E A L V L S D R A P F A A

P S P F A E L V L P P Q Q

Recombinant PD-ECGF was sequenced at the DNA level and gene contains the nucleotide sequence of the polypeptide and flanking regions which are indicated below:

this process, e.g. fibroblast growth factors, transforming growth factor-α and -β, tumour necrosis factor, and angiogenin (Folkman el al., supra; Frater-Schroder et al., 1987; Leibovich et al., supra). These factors elicit

```
GGGCAGTGGA CCGCTGTGCG CGAACCCTGA ACCCTACGGT        40
CCCGACCCGC GGGCGAGGCC GGGTACCTGG GCTGGGATCC        80
GGAGCAAGCG GGCGAGGGCA GCGCCCTAAG CAGGCCCGGA       120
GCG ATG GCA GCC TTG ATG ACC CCG GGA ACC GGG       153
GCC CCA CCC GCG CCT GGT GAC TTC TCC GGG GAA       186
GGG AGC CAG GGA CTT CCC GAC CCT TCG CCA GAG       219
CCC AAG CAG CTC CCG GAG CTG ATC CGC ATG AAG       252
CGA GAC GGA GGC CGC CTG AGC GAA GCG GAC ATC       285
AGG GGC TTC GTG GCC GCT GTG GTG AAT GGG AGC       318
GCG CAG GGC GCA CAG ATC GGG GCC ATG CTG ATG       351
GCC ATC CGA CTT CGG GGC ATG GAT CTG GAG GAG       384
ACC TCG GTG CTG ACC CAG GCC CTG CCT CAG TCG       417
GGA CAG CAG CTG GAG TGG CCA GAG GCC TGG CGC       450
CAG CAG CTT GTG GAC AAG CAT TCC ACA GGG GGT       483
GTG GGT GAC AAG GTC AGC CTG GTC CTC GCA CCT       516
GCC CTG GCG GCA TGT GGC TGC AAG GTG CCA ATG       549
ATC AGC GGA CGT GGT CTG GGG CAC ACA GGA GGC       582
ACC TTG GAT AAG CTG GAG TCT ATT CCT GGA TTC       615
AAT GTC ATC CAG AGC CCA GAG CAG ATG CAA GTG       648
CTG CTG GAC CAG GCG GGC TGC TGT ATC GTG GGT       681
CAG AGT GAG CAG CTG GTT CCT GCG GAC GGA ATC       714
CTA TAT GCA GCC AGA GAT TGT ACA GCC ACC GTG       747
GAC AGC CTG CCA CTC ATC ACA GCC TCC ATT CTC       780
AGT AAG AAA CTC GTG GAG GGG CTG TCC GCT CTG       813
GTG GTG GAC GTT AAG TTC GGA GGG GCC GCC GTC       846
TTC CCC AAC CAG GAG CAG GCC CGG GAG CTG GCA       879
AAG ACG CTG GTT GGC GTG GGA GCC AGC CTA GGG       912
CTT CGG GTC GCG GCA GCG CTG ACC GCC ATG GAC       945
AAG CCC CTG GGT CGC TGC GTG GGC CAC GCC CTG       978
GAG GTG GAG GAG GCG CTG CTC TGC ATG GAC GGC      1011
GCA GGC CCG CCA GAC TTA AGG GAC CTG GTC ACC      1044
ACG CTC GGG GGC GCC CTG CTC TGG CTC AGC GGA      1077
CAC GCG GGG ACT CAG GCC CAG GGC GCT GCC CGG      1110
GTG GCC GCG GCG CTG GAC GAC GGC TCG GCC CTT      1143
GGC CGC TTC GAG CGG ATG CTG GCG GCG CAG GGC      1176
GTG GAT CCC GGT CTG GCC CGA GCC CTG TGC TCG      1209
GGA AGT CCC GCA GAA CGC CGG CAG CTG CTG CCT      1242
CGC GCC GGG GAG CAG GAG GAG CTG CTG GCG CCC      1275
GCA GAT GGC ACC GTG GAG CTG GTC CGG GCG CTG      1308
CCG CTG GCG CTG GTG CTG CAC GAG CTC GGG GCC      1341
GGG CGC AGC CGC GCT GGG GAG CCG CTC CGC CTG      1374
GGG GTG GCG GCA GAG CTG GTC GTG GGT          1407
CAG AGG CTG CGC CGT GGG ACC CCC TGG CTC CGC      1440
GTG CAC CGG GAC GGC CCC GCG CTC AGC GGC CCG      1473
CAG AGC CGC GCC CTG CAG GAG GCG CTC GTA CTC      1506
TCC GAC GCG CCA TTC GCC GCC CCC TTG CCC         1539
TTC GCA GAG CTC GTT CTG CCG CCG CAG CAA TAA      1572
AGC TCC TTT GCC GCG AAA AAA AAA A            1597
```

PD-ECGF stimulates chemotaxis and proliferation of endothelial cells in vitro, and induces angiogenesis in vitro. Angiogenesis, the formation of new capillary blood vessels by sprouting from preexisting vessels, is an important process in embryogenesis would healing, and organ regeneration. In addition, aberrant angiogenesis occurs in several pathological conditions, such as in tumor growth, in certain retinopathies, and in rheumatoid arthritis. Angiogenesis is a complex process that involves several steps, including migration and proliferation of endothelial cells (Folkman et al., supra). Certain polypeptide factors have been identified that stimulate the angiogenic response either directly by virtue of their mitogenic and/or chemotactic activity for endothelial cells or by as yet unknown indirect mechanisms. Unlike these factors which have multiple effects on a wide variety of cell types, a human platelet-derived endothelial cell growth factor (PD-ECGF) specifically stimulates the growth of endothelial cells in vitro (Miyazono et al., J. Biol. Chem. 262: 4098–4103 (1987) e.g. it does not stimulate growth of fibroblasts. PD- ECGF is a 45 kDa protein distinct from previously known growth factors.

Endothelial cell growth factor is useful in inducing angiogenesis, accelerating wound healing, preventing atherosclerosis, and treating thrombocytopenia by administering a therapeutic amount to a mammal. It is preferred that homogeneous or recombinant PD-ECGF be administered in therapeutic amounts to mammals including humans.

PD-ECGF also stimulates endothelial cell chemotaxis in vitro and induces angiogenesis in vitro in endothelial cells, especially the chick chorioallantoic membrane (CAM). Antibodies against the factor, which neutralize its mitogenic activity in vitro, also greatly inhibited the angiogenic response. Thus, PD-ECGF is a novel angiogenic factor exhibiting target cell specificity towards endothelial cells.

To identify the chemotactic domain of PD-ECGF that induces endothelial cell chemotaxis in vitro, proteolytic fragments of PD-ECGF are tested for their ability to induce chemotactic responses of endothelial cells as described. Proteolytic fragments are prepared by enzymatic or chemical hydrolysis of PD-ECGF, especially by serine proteases-like trypsin, by V8 protease and by CNBr-induced cleavage. Fragments are purified by reverse phase HPLC. The fragments are then tested in chemotaxis assays with mammalian endothelial cells, especially bovine and porcine cells. The chemotaxis assay is the same that is used for testing the chemotactic activity of native or recombinant PD-ECGF.

The present invention shows that PD-ECGF is an angiogenic factor of a novel type. Stimulation of growth and chemotaxis of endothelial cells are in vitro properties that PD-ECGF has in common with other known angiogenesis factors (e.g. the FGFs). In contrast to these, however, PD-ECGF shows target cell specificity for endothelial cells in proliferation as well as chemotaxis assays. Thus, it can specifically and directly induce endothelial responses that are crucial for angiogenesis. PD-ECGF is the only endothelial mitogen present in a platelet lysate and may thus be an important factor involved in platelet mediated processes such as wound healing and the vascularization of thrombi. In addition, it may be of considerable importance as an intraluminal factor capable of regulating endothelial cell turnover if released from platelets. Endothelial cell proliferation inside larger vessels is important for the regeneration of damaged endothelium and thus probably important for the prevention of atherosclerosis. The availability of functionally active recombinant PD-ECGF combined with a high yield purification method, cDNA clones and specific antibodies will now made it possible to address questions related to the in vitro function of PD-ECGF, and to provide sufficient PD-ECGF for therapeutic use.

EXAMPLES

Cell Cultures and Media

Endothelial cells were collected from a fresh porcine aorta using collagenase digestion as described by Booyse et al. Thrombi. diathes. haemorrh 34: 825 (1975). Cloning of the endothelial cells was performed by single cell platings as described originally by Puck et al. J. Exp. Med. 103: 273 (1956). The endothelial cells were maintained in 25 cm$^2$ culture flasks in Ham's F-10 medium containing 10% fetal bovine serum (FBS) and antibiotics, and subcultured using 0.25% trypsin solution (Gibco) when the cells reached confluency. There was no evidence of transformation or loss of the endothelial monolayer under these conditions for more than six months. Normal rat kidney (NRK) fibroblasts were obtained by the method described by Duc-Nguyen et al. J. Bacterial 92: 1133 (1966) and subcultured in Dulbecco's modified Eagle medium containing 10% FBS.

Cell Number Determination

For growth experiments, endothelial cells were subcultured at a plating density of 20,000 cells/dish in a 35-mm tissue culture dish (Corning) using Ham's F-10 medium containing 10% FBS. The cells were incubated for 24 h to allow for attachment, and then the medium was changed to the test media. The cells were removed from the dishes by incubating for 15 min. in trypsin-EDTA and cell number was determined in duplicate. The cultures were refed with fresh test media on Day 4.

Preparation of Platelet Lysate

Blood was collected from normal volunteers in citrate-phosphate-dextrose solution, and fresh platelet-rich plasma was obtained by centrifugation at 160 g for 20 min at 20° C. The upper four-fifths portion of platelet-rich plasma was centrifuged at 1,700 g for 20 min. at 20° C., and the platelet pellet was suspended in 10 mM Tris HCl (pH 7.4)/150 mN NaCl/0.01 % polyethylene glycol (PEG). The platelets were washed twice with the same buffer in the centrifuge and sonicated for 1 min. By this method, erythrocyte and leukocyte contamination in the last platelet suspension was less than 0.1%. Sonicated platelets were centrifuged at 48,000 g for 30 min. at 4° C. and the supernatants were used as platelet lysate. About 2 ml of platelet lysate was obtained from 200 ml of whole blood. Further operations were performed at 4° C., unless otherwise specified.

Assay for Growth Promoting Activity

Growth promoting activity was determined by using porcine aortic endothelial cells as indicator cells, as previously has been described (Miyazono et al., Biochem. Biophys. Res. Commun. 126: 83–88 (1985); Exp. Cell Res. 159: 487–494 (1985)). Endothelial cells, cultured in Ham's F10 medium supplemented with 10% fetal bovine serum (Flow Laboratories) and antibiotics, were subcultured weekly at a ratio of 1 to 20. For mitogenic assay, the cells were trypsinized and re-plated sparsely (approximately $1 \times 10^4$ cells per well) with 500 ul of Ham's F-10 medium containing 0.5% fetal bovine serum and antibiotics in 24-well tissue culture plates (16 mm diameter, Costar). After 24 h of incubation, the test samples were added to the wells. 18 h later, [$^3$H]-thymidine (0.2 uCi/well; 6.7 Ci/mM, New England Nuclear) was added. After an additional 4 h, the cells were fixed with ice cold 5% (w/v) trichloroacetic acid for 20 min. The resulting precipitates were washed extensively with water and solubilized with 200 ul of 1M NaOH. After mixing at room temperature for 20 min, 200 ul of 1M HCl was added to the wells. [$^3$H]-radioactivity was then determined in a liquid scintillation counter using 20 ml of Instagel (Packard) per sample.

Purification of Platelet-Derived Endothelial Cell Growth Factor from Human Platelets Assay—Growth factor activity was monitored throughout the purification procedures using porcine aortic endothelial cells as target cells as described above.

Growth promoting activity on human foreskin fibroblasts was assayed by the method by Betsholtz and Westermark J. Cell Physiol. 18: 203-210 (1984).

General—During the purification, plastic utensils were used to decrease the loss of activity by adsorption to glass surfaces. All operations were performed at 4° C., unless otherwise specified. Protein concentration was determined by the dye fixation assay of Bradford Anal. Biochem. 72: 248-254 (1976), unless otherwise specified.

Preparation of Platelet Lysate—For the purification of endothelial cell growth factor, a side fraction from the purification of platelet-derived growth factor (PDGF) from human platelets (Heldin et al., Meth. Emzymal. 147: 3-13 (1987)) was used. The first step in the purification of PDGF from platelet pellets is a chromatography on CM-Sephadex. The cationic PDGF is adsorbed to this column. Since endothelial cell growth factor in human platelets is an anionic protein, it was not adsorbed to the CM-Sephadex column in the initial step of the purification of PDGF (Heldin et al., supra). As expected, the flow-through fraction was found to contain growth promoting activity for endothelial cells, and was used as starting material in the purification. About 15 liters of the non-adsorbed fraction were processed at a time; this was derived from about 900 l of fresh human blood. The non-adsorbed fraction can be stored in 5 l containers at −20° C. for up to 10 years until used.

QAE-Sephadex Chromatography—The non-adsorbed fraction from CM-Sephadex chromatography was thawed and processed to QAE-Sephadex chromatography. Dry QAE-Sephadex gel (0.7 g/l; A-50, Pharmacia) was added and mixed by shaking overnight. The gel was then allowed to sediment and, after the non-adsorbed fraction was discarded, it was poured into a column (60×5 cm, Pharmacia). The column was washed with 4 l of 75 mM NaCl in 10 mM phosphate, pH 7.4, and eluted with 2.5 l of 250 mM NaCl in 10 mM phosphate, pH 7.4.

The bulk of the activity bound to this column and eluted between 75 and 250 mM NaCl at pH7.4. This resulted in a 25-fold purification estimated by the protein recovered, and an assumed recovery of 80% in this step. Since the growth promoting activity in the starting material was variable, maybe due to the presence of inhibitory substances (see below), the yield in this step could not be determined exactly.

Ammonium Sulfate Precipitation—Ammonium sulfate (247 g/l, 42 % of saturation) was added to the eluate of QAE-Sephadex chromatography. After equilibration for 2 h at 4° C., the sample was centrifuged at 2,075×g for 15 min. The precipitate was collected by centrifugation and resuspended in 50 mM NaCl in 10 mM bis(2-hydroxylethyl) amino-tris-(hydroxymethyl)methane (Bis-Tris), pH 7.0.

At neutral pH, 42% saturation of ammonium sulfate precipitated about 90% of the activity, while only 9% of protein was coprecipitated. This procedure led to a 10-fold purification with about 700 mg of protein remaining in 200 ml of volume.

DEAE-Sepharose Chromatography—The material obtained by ammonium sulfate precipitation (approximately 700 mg of protein in the volume of 200 ml) was treated with 5mM dithiothreitol at room temperature for 2 h. The sample was then dialyzed extensively against 50 mM NaCl in 10 mM Bis-Tris, pH 7.0, and applied to a column of DEAE-Sepharose CL-6B (40 ml; Pharmacia). The column was washed with 100 ml of 50 mM NaCl in 10 mM Bis-Tris buffer, pH 7.0, and eluted with a linear gradient (800 ml) of NaCl from 50 to 200 mM in 10 mM Bis-Tris, pH 7.0, at a flow rate of 120 ml/hr. Fractions of 20 ml were collected and analyzed for protein and growth promoting activity.

The endothelial cell growth promoting activity eluted at about 120-150 mM of NaCl at pH 7.0. This step led to a further 6-fold purification at a recovery of 50% (FIG. 1).

Hydroxylapatite Chromatography

The active fractions from DEAE-Sepharose chromatography (approximately 60 mg of protein) were combined and loaded directly onto an 8 ml column of hydroxylapatite (Clarkson Chemical Co.: Williamsport, Pa.) equilibrated with 50 mM NaCl, 0.6 mM phosphate, pH 7.4. The column was washed with 80 ml of the same buffer, eluted with 50 mM NaCl, 15 mM phosphate, pH 7.4, followed by 200 mM phosphate, pH 7.4. Fractions of 8 ml were assayed for protein and growth promoting activity.

Figure 2:
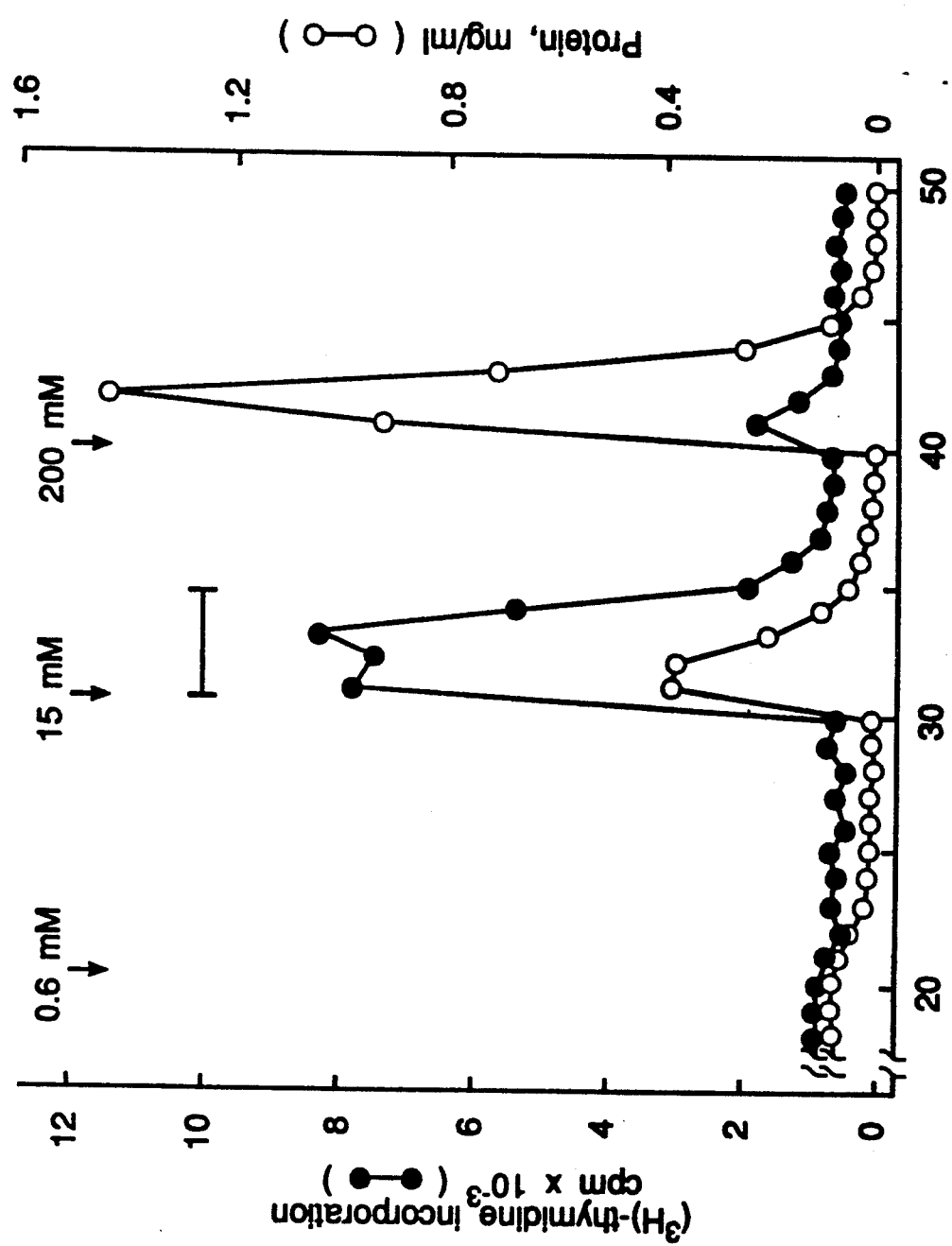
FIG. 2. Chromatographic purification of human PD-ECGF on hydroxylapatite.

Hydroxylapatite chromatography gave a further 4-fold increase in specific activity (FIG. 2). Almost all the protein bound to the gel, and the growth promoting activity eluted at 15 mM phosphate, whereas the bulk of protein eluted at a higher concentration of phosphate. The recovery of the activity was about 55% in this step, and about 8 mg of protein remained.

Final purification of the growth factor was achieved using ion exchange and high-resolving gel chromatography columns attached to a fast-performance liquid chromatography (FPLC) apparatus.

Mono Q Chromatography

The active fractions of the hydroxylapatite chromatography were pooled, centrifuged at 90,000×g for 30 min at 4° C., and applied directly to a Mono Q column (HR 5/5, Pharmacia). This column and the following two (TSK-G4000 SW and Superose 12), were attached to an FPLC-apparatus (Pharmacia) and operated at room temperature. The column was eluted at a flow rate of 1 ml/min with a gradient of 0-500 mM NaCl in 10 mM Bis-Tris, pH 7.0. Absorbance at 280 nm was monitored. Fractions of 1 ml were collected and tested for growth promoting activity.

Figure 3:
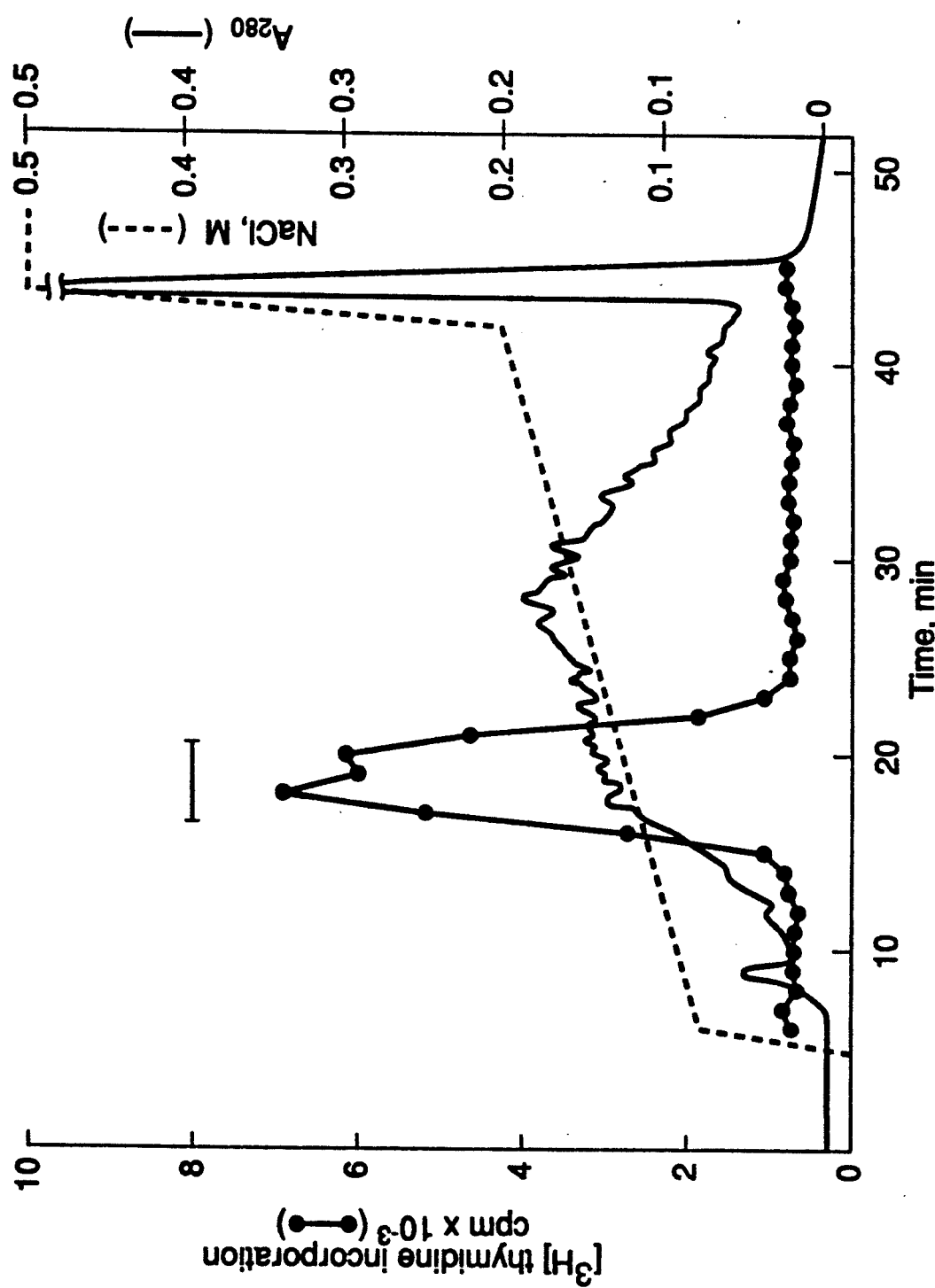
FIG. 3. Chromatographic purification of human PD-ECGF on a Mono Q column.

A single peak of growth promoting activity was obtained at 120 mM NaCl at pH 7.0 (FIG. 3). This step led to a further 4-fold purification with 50% of recovery.

TSK-G4000 SW Gel Chromatography

The active fractions obtained from Mono Q column chromatography were pooled, lyophilized without prior dialysis and dissolved in 200 ul of water. The aliquot was then applied to a TSK-G4000 SW column (7.5×600 mm, LKB) with a precolumn (Ultropac column, 7.5×75 mm, LKB). The column was equilibrated with 100 mM phosphate, pH 6.5, and eluted at a flow rate of 500 ul/min. The absorbance of the column effluent was monitored at 280 nm. Each 500 ul fraction was collected and tested for growth promoting activity.

Figure 4:
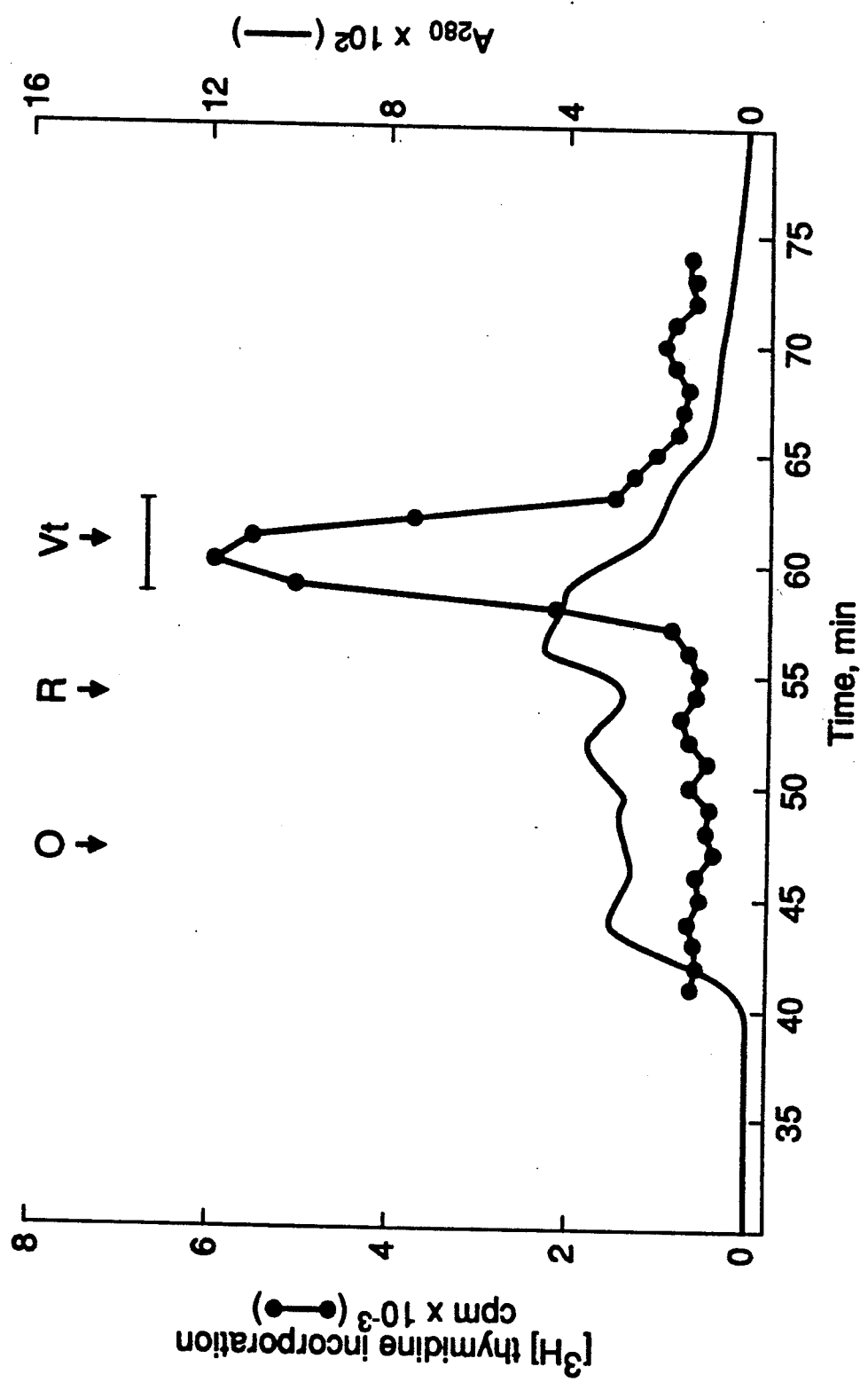
FIG. 4. Chromatographic purification of human PD-ECGF on a TSK-G4000 SW column.

The result was a single broad peak of activity eluting anomalously late, at a position corresponding to a $M_r$ of less than 12,000 (FIG. 4). The recovery of the activity was 30% giving a 4-fold increase in specific activity.

Superose 12 Gel Chromatography

The active fractions obtained from TSK-G4000 SW chromatography were pooled, dialyzed using Spectrapor dialysis tubing (Mr cutoff, 3,500, Spectrum Medical Industries, Inc.) against 100 mM NaCl, 10 mM 4-(2-hydroxyethyl)-1-piperazine-ethanesulfonic acid (Hepes), pH 7.0, and then lyophilized. The material was resuspended in 100 ul of water and run on a Superose 12 column (HR 10/30, Pharmacia) in 200 mM NaCl, 10 mM Hepes, pH 7.0. The column was eluted at a flow rate of 400 ul/min and monitored with the absorbance at 280 nm. Fractions of 200 ul were collected and assayed for growth promoting activity.

Figure 5A:
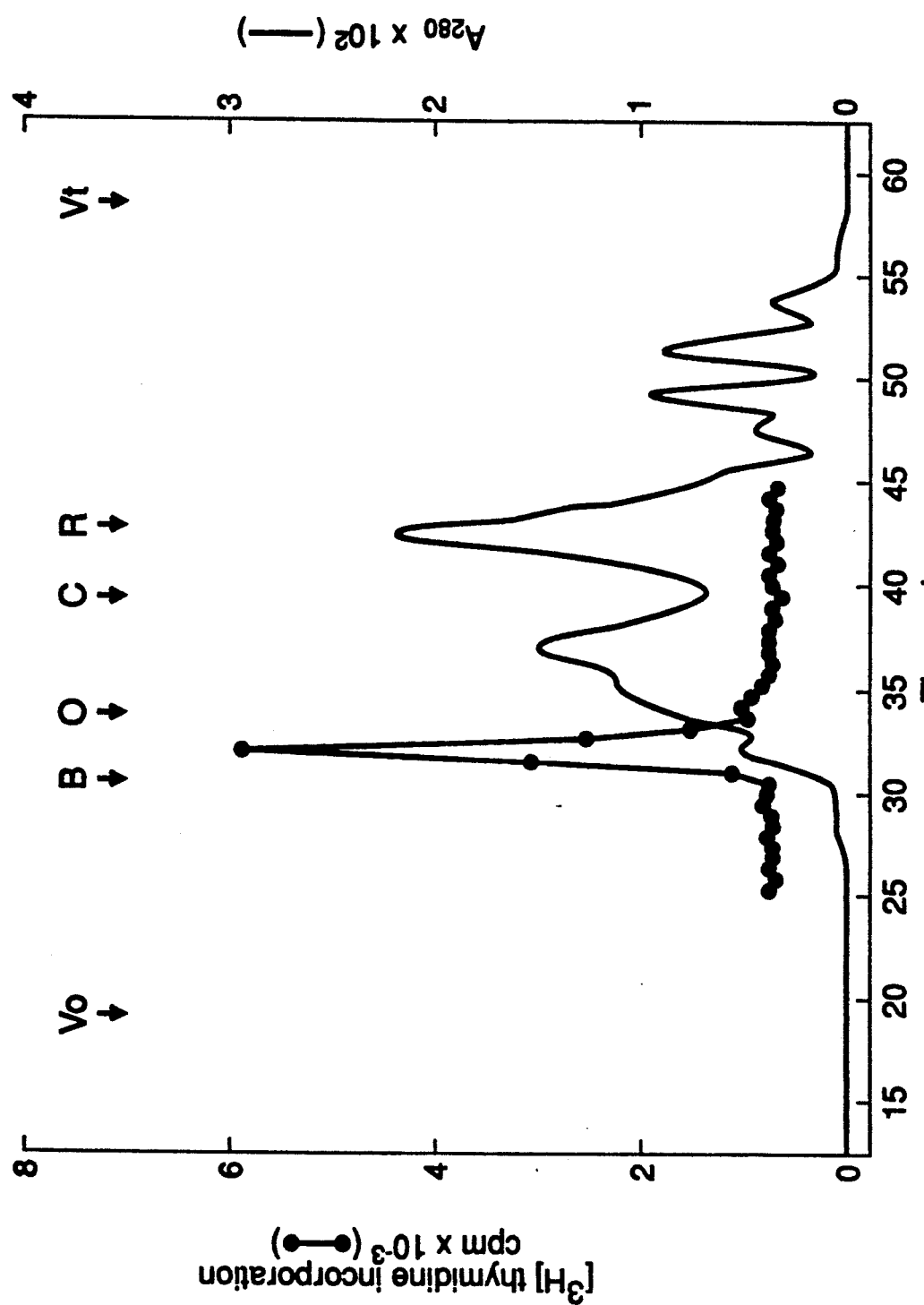
FIG. 5A-C. Chromatographic purification of human PD-ECGF on a Superose 12 column. A) Column profile. B) SDS polyacrylamide gel of purified fractions of human PD-ECGF. C) SDS polycrylamide gel of pure PD-ECGF in the presence or absence of a reducing agent.

This procedure yielded a single sharp peak of bioactivity with an elution position between bovine serum albumin and ovalbumin, well separated from the majority of protein (FIG. 5A). The increase in specific activity was 12-fold in this step at 30% recovery, giving 2 ug of pure material. The protein concentration in the purified fraction was estimated by comparing the intensity of the bands after sodium dodecyl sulfate (SDS)-gel electrophoresis and silver staining, with those of standards of bovine serum albumin.

Figure 5B:
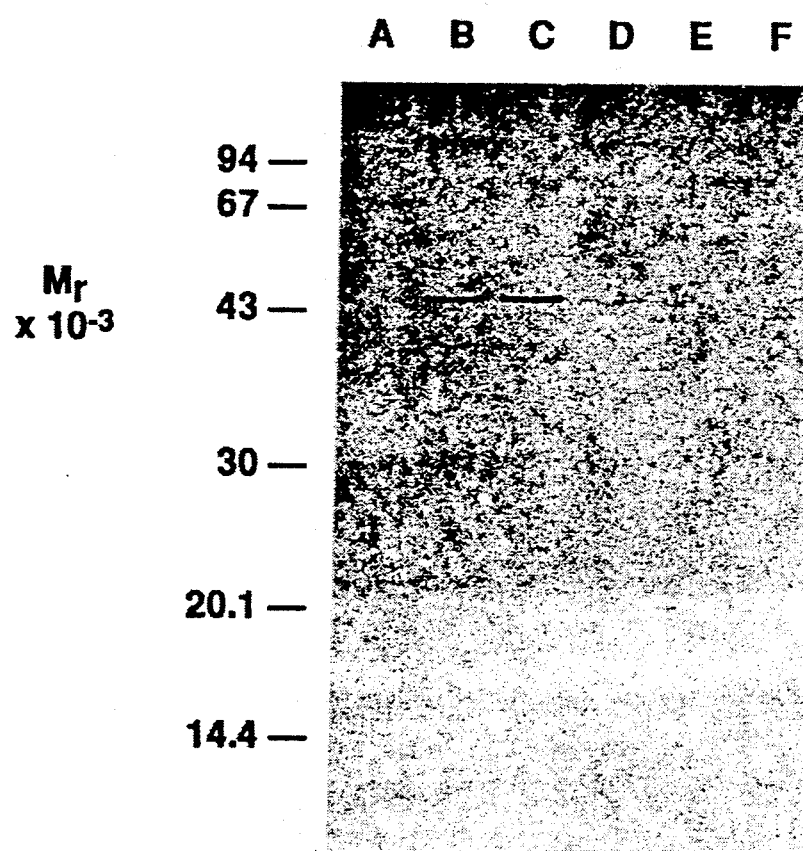
Figure 5C:
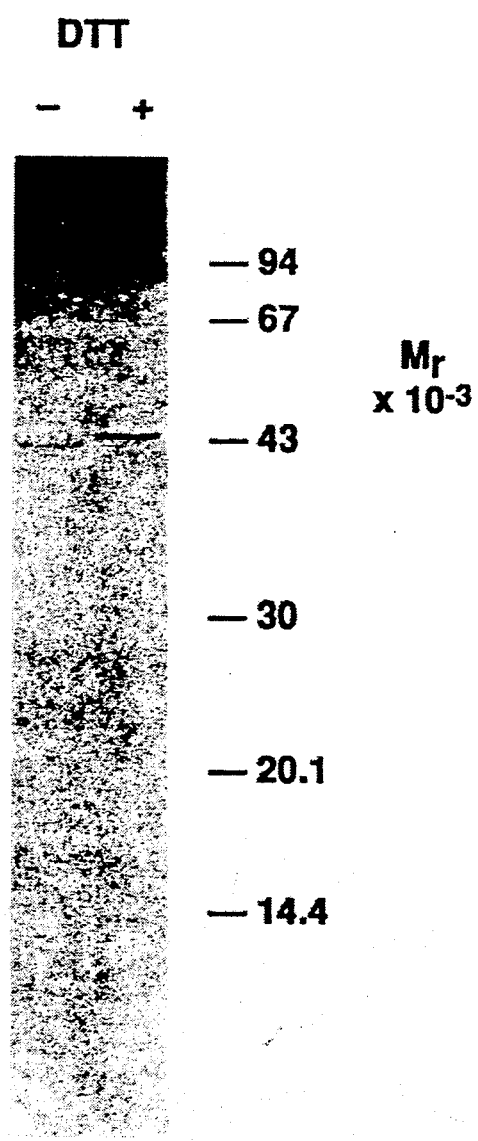

The protein compositions of the fractions from the Superose 12 chromatography step were analyzed by SDS-gel electrophoresis and silver staining (FIG. 5B). A homogenous protein with a $M_r$ of 45,000 exactly coeluted with the growth promoting activity, suggesting that it represents the growth factor. A similar mobility was observed when the samples were analyzed under non-reducing conditions (FIG. 5C), suggesting that the endothelial cell growth factor from platelets is composed of a single polypeptide chain.

A summary of the purification procedure from 200 g of platelet protein is shown in Table 1. The overall increase in activity was about 1,000,000-fold at a recovery of 1%.

TABLE 1

Summary of the Purification of Platelet-Derived Endothelial Cell Growth Factor

| purification step | protein (ug) | max stimulation (ng/mL) | purification (x-fold) | yield (%) |
|---|---|---|---|---|
| platelet lysate (flow-through from CM-Sephadex) | 200 000 000 | a | 1 | 100 |
| QAE-Sephadex | 8 000 000 | 1 000 000 | 20[a] | 80[a] |
| ammonium sulfate pptn | 700 000 | 100 000 | 200 | 70 |
| DEAE-Sepharose | 60 000 | 17 000 | 1 200 | 36 |
| hydroxyapatite | 8 000 | 4 000 | 5 000 | 20 |
| Mono Q | 1 000 | 1 000 | 20 000 | 10 |
| TSK-G4000 SW | 70 | 240 | 83 000 | 3 |
| Superose 12 | 2[b] | 20 | 1 000 000 | 1 |

[a]The growth promoting activity in the platelet lysate was variable, maybe due to the presence of growth inhibitors (see, discussion). Therefore, the specific activity of the starting material could not be accurately determined. The purification in the QAE step was estimated at 20-fold, based on the amount of protein recovered and an assumed recovery of 80% of activity in this step.
[b]Protein concentration was estimated by the relative intensities of bands in silver stained SDS-gels.

Improved Purification Protocol for PD-ECGF

The initial steps of the prufication were performed as described above As the next step, chrmoatography on an HPLC-grade hydroxylapatite column was used.

Chromatography on a High-Performance Hydroxylapatite Column.

The material obtained from DEAE-Sepharose chromatography was filtered through a 0.22 um filter (Millipore) and loaded at room temperature onto a high-performance hydroxylapatite column (100×7.8 mm; Bi-oRad) equipped with a guard column (50×4.0 mm; Bio-Rad). The column was preequilibrated with 1 mM phosphate buffer, pH 6.8, 50 mM NaCl, and 0.01 mM $CaCl_2$ and eluted at a flow-rate of 0.5 mL/min with a gradient of 1–100 mM phosphate, pH 6.8, 50 mM NaCl, and 0.01 mM $CaCl_2$. The column was then washed with 1M phosphate buffer, pH 6.8, and 0.01 mM $CaCl_2$. Fractions of 1 mL were collected and tested for growth-promoting activity on porcine endothelial cells.

Figure 6A:
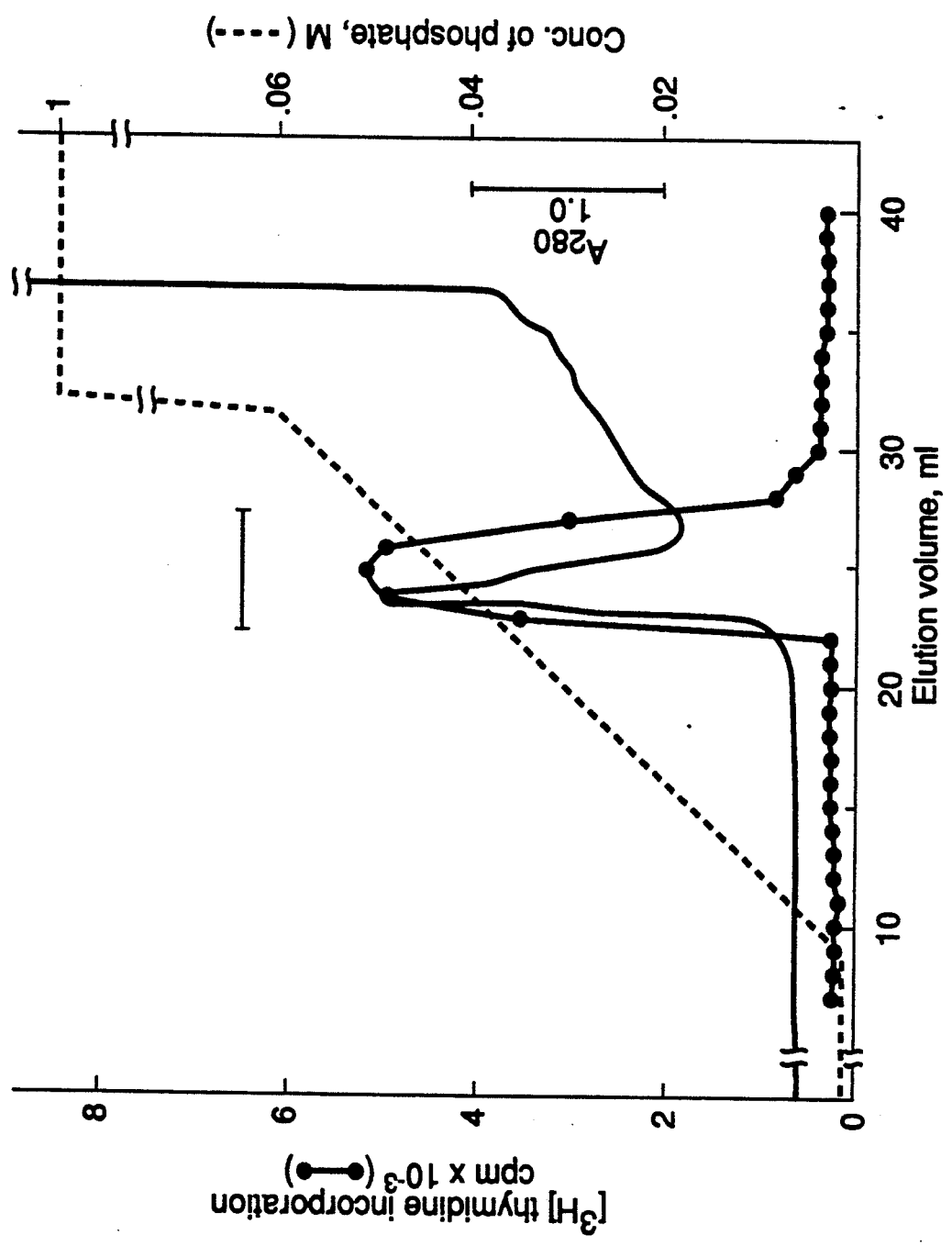
FIG. 6A-B. Chromatographic purification of human PD-ECGF on a high-performance hydroxylapetite column. A) Column profile. B) Analysis of fractions by SDS gel electrophoresis and silver staining.
Figure 6B:
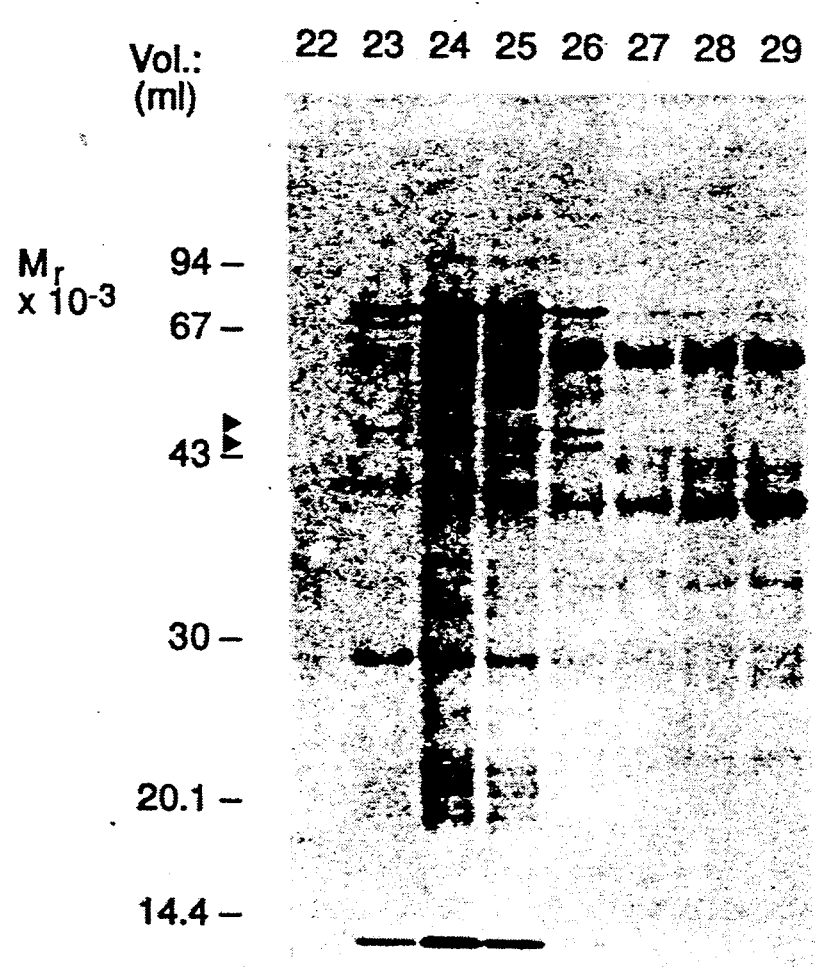

PD-ECGF bound to the gel in 1 mM phosphate buffer, pH 6.8, and was eluted with a linear gradient of phosphate (as indicated in FIG. 6A). The recovery of activity was about 32% in this step. Individual fractions from the chromatogram were analyzed by SDS gel electrophoresis and silver staining; the growth-promoting activity coeluted with two components of 46 and 44 kDa and some other components (FIG. 6B).

Chromatography on an Alkyl-Superose Column

Figure 7A:
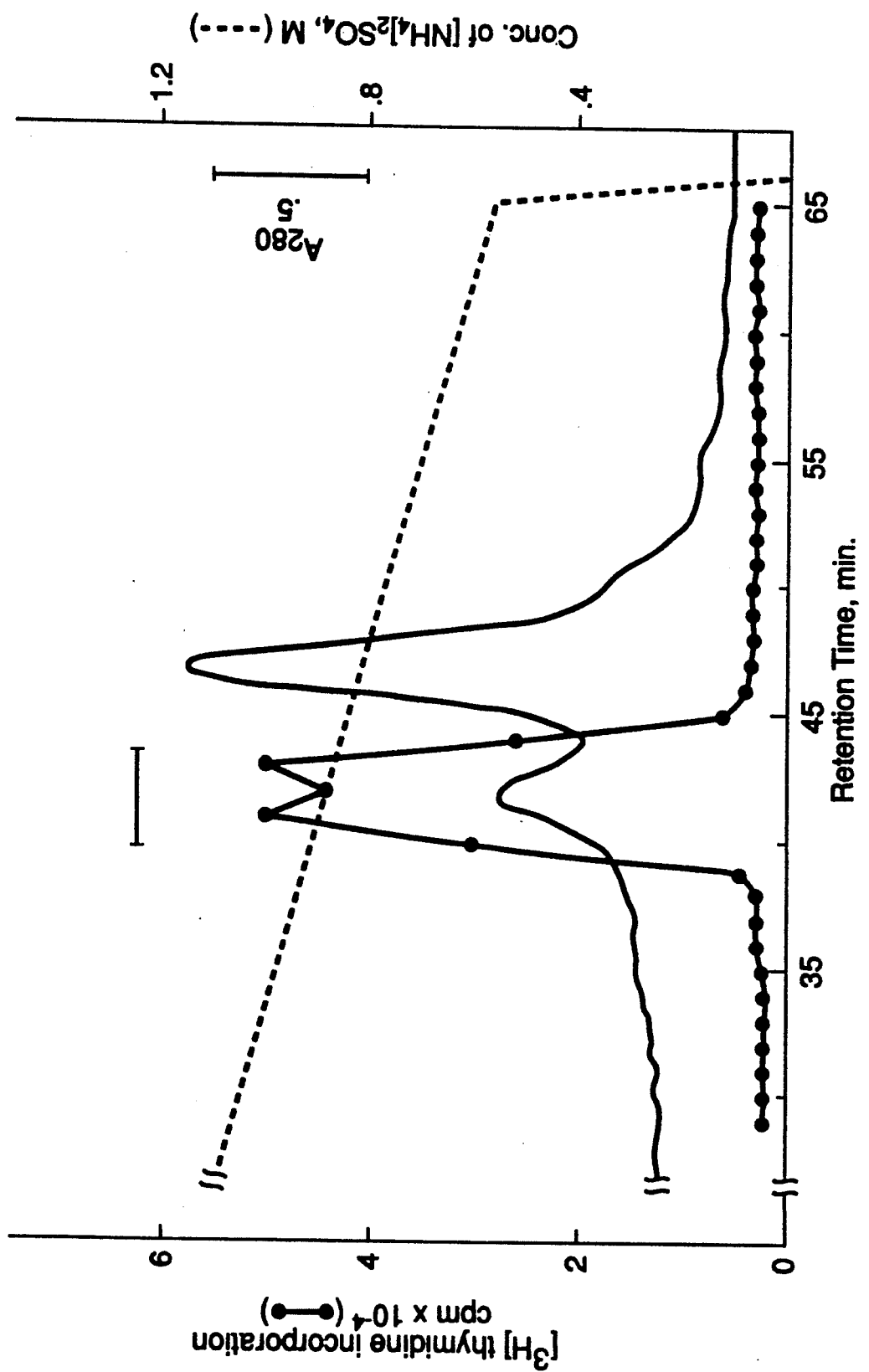

The active fractions from the high-performance hydroxylapatite chromatography were pooled and mixed with an equal volume of 2.8M ammonium sulfate (HPLC-grade, Bio-Rad) and 100 mM phosphate buffer, pH 6.8. The material was applied to an alkyl-Superose column (HR5/5, Pharmacia), preequilibrated with 1.4M ammonium sulfate/100 mM phosphate buffer, pH 6.8, and eluted with a gradient of ammonium sulfate from 1.4 to 0M in 100 mM phospate buffer, pH 6.8 as indicated in FIG. 7A. The flow-rate was 0.5 ml/min and the column was operated at room temperature. The absorbance of the column effluent was monitored at 280 nm. Fractions of 500 ul were collected and assayed for grwoth-promoting activity.

Final purification was achieved by hydrophobic chromatography using FPLC. The pooled fractions from the high-performance hydroxylapatite chromatography were applied to an alkyl-Superose column, equilibrated with 1.4M ammonium sulfate/100 mM phosphate buffer, pH 6.8, and eluted with a decreasing gradient of ammonium sulfate in 100 mM phosphate buffer, pH 6.8. A single peak of growth-promoting activity was obtained at about 0.8M ammonium sulfate (FIG. 7A). The increase in specific activity was 50-fold in this step at a recovery of 82%. The protein compositions of individual fractions of the alkyl-Superose chromatogram were analyzed by SDS gel electrophoresis and silver staining (FIG. 7B); again, the active fractions contained the principal two components of 46 and 44 kDa, indicating that PD-ECGF was essentially pure. Furthermore, a very faint band of $M_r$ 42,000 was reproducibly found. The proportion of these proteins in the silver-stained gels differed from preparation to preparation, but the 46- and 44-kDa components were always predominant.

A summary of the purification procedure starting from 300 g of platelet protein, corresponding to approximately 800–1,000L of human blood, is shown in Table 2. About 34 ug of pure PD-ECGF was obtained from each preparation. The material was purified 1,250,000-fold at an overall yield of about 14%.

TABLE 2

Summary of the Purification of PD-ECGF[a]

| purification step | protein (ug) | max stimulation (ng/mL) | purification (x-fold) | yield (%) |
|---|---|---|---|---|
| platelet lysate (flow-through from CM-Sephadex) | 300 000 000 | [b] | 1 | [b] |
| QAE-Sephadex | 12 000 000 | 1 000 000 | 20[b] | 80 |
| ammonium sulfate pptn | 800 000 | 80 000 | 250 | 58 |
| DEAE-Sepharose | 80 000 | 10 000 | 2 000 | 53 |
| high-performance hydroxyapatite | 2 000 | 800 | 25 000 | 17 |
| alkyl-Superose | 34[c] | 16 | 1 250 000 | 14 |

[a]The results represent mean values of four individual preparations.
[b]The growth-promoting activity in platelet lysate was variable, maybe due to the presence of growth inhibitors (Miyazono, et al., 1987). Therefore, the purification in the QAE-Sephadex chromatography was estimated at 20-fold on the basis of the amount of protein recovered and an assumed recovery of 80% of activity Mizayzono et al, J. Biol. Chem 262: 4098-4103 (1987).
[c]Protein concentration was determined by amino acid analysis.

SDS-Gel Electrophoresis

SDS-gel electrophoresis was performed according to the method described by Blobel and Dobberstein J. Cell Biol. 67: 838-851 (1975). Briefly, samples were heated (95° C., 3 min.) with or without 10 mM dithiothreitol, and applied to a gradient gel consisting of 10-18% polyacylamide. The gel was fixed with glutaraldehyde after electrophoresis and then silver stained following morrisey, Anal. Biochem. 117: 307-310 (1981). $M_r$ markers (Pharmacial) containing phosphorylase b (94,000), bovine serum albumin (67,000), ovalbumin (43,000), carbonic anhydrase (30,000), soybean trypsin inhibitor (20,100) and a-lactalbumin (14,400) were used.

Structural Analysis and Amino Acid Sequence of PD-ECGF

About 40 ug of pure PD-ECGF was reduced and pyridyl-ethylated, and then desalted using narrow-bore reversed phase HPLC. The material was then subjected to tryptic digestion followed by separation of the fragments on a narrow-bore reversed-phase HPLC column eluted in 0.1% trifluoroacetic acid with a gradient of acetonitrile.

For reduction and pyridyl-ethylation, PD-ECGF was first desalted on a C4 column and then dried in a Speedivac Concentrator and redissolved in 200 ul of 6 M guanidine HCl, 0.25 M Tris-HCl, pH 8.5 and 2 mM EDTA, containing 100 ug of dithiothreitol. The solution was flushed with nitrogen for 20 s and left at room temperature for 3 h, at which time 2 ul of 4-vinyl-pyridine was added. After another three hours at room temperature, the sample was desalted by chromatography on the C4 column in the trifluoracetic acid/acetonitrile buffer system. The volatile solvent was removed as above and PD-ECGF was digested with TPCK-Trypsin (Sigma; enzyme to substrate ratio, 1/50 (w/w)) in 0.1 M ammonium bicarbonate, containing 2 M urea, for 4 h at 37° C. The tryptic fragments were immediately loaded onto a narrow bore reversed-phase HPLC. The chromatographic equipment consisted of a dual pump LKB system, adapted for narrow bore chromatography and equipped with a variable wavelength detector. The column temperature was kept at 35° C., the flow rate was 100 ul/min and the effluents were monitored at 220 nm. Fractions were collected manually in polypropylene tubes.

Figure 8A:
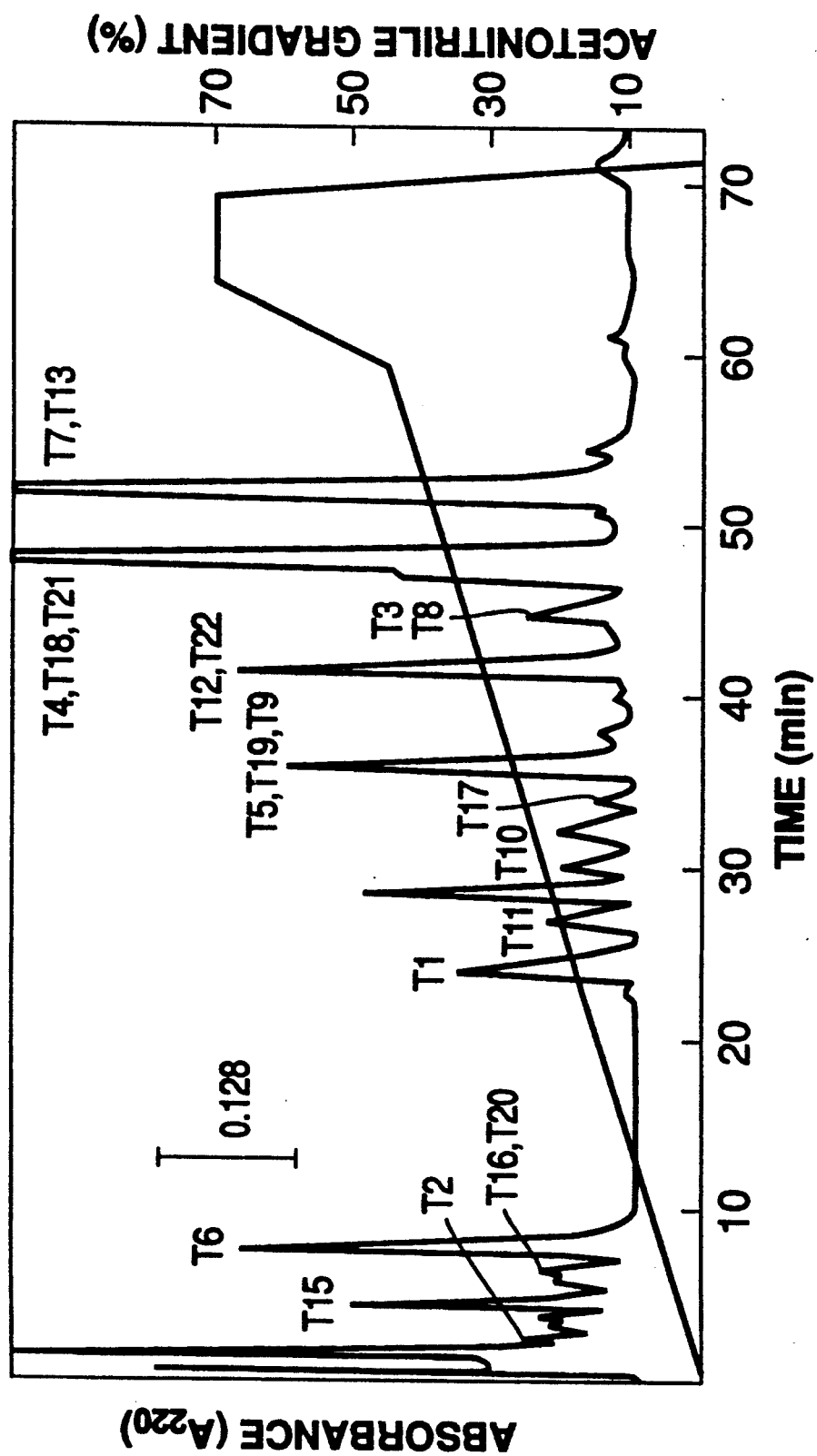
FIG. 8A-C. Separation of tryptic peptide fragments of human PD-ECGF by narrow-bore reversed phase HPLC.

The separation of tryptic fragments of PD-ECGF is illustrated in FIG. 8A. Approximately 40 ug of trypsin-digested PD-ECGF was loaded onto a C4 reversed phase column (Brownlee Aquapore BU-300; 2.1×30 mm and eluted with a linear gradient of acetonitrile in 0.1% trifluoracetic acid.

Figure 8C:
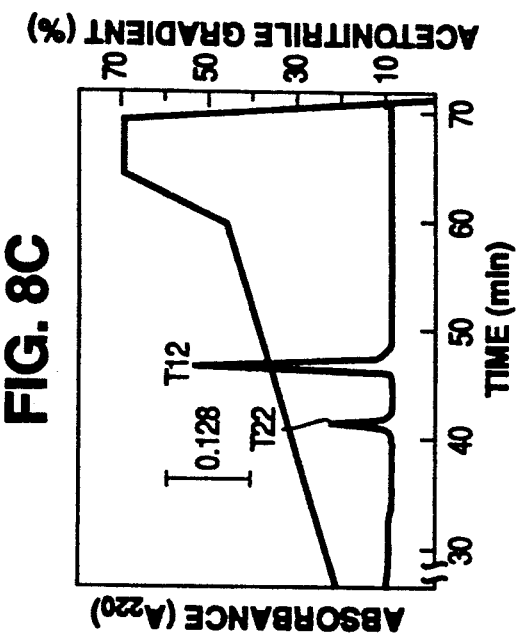
Figure 8E:
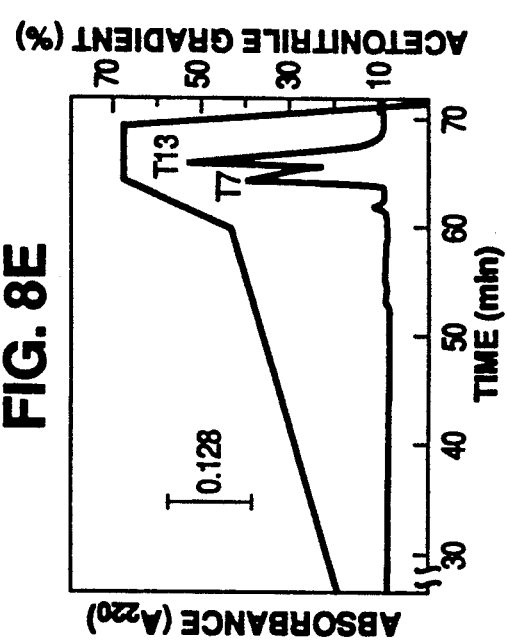
Figure 8B:
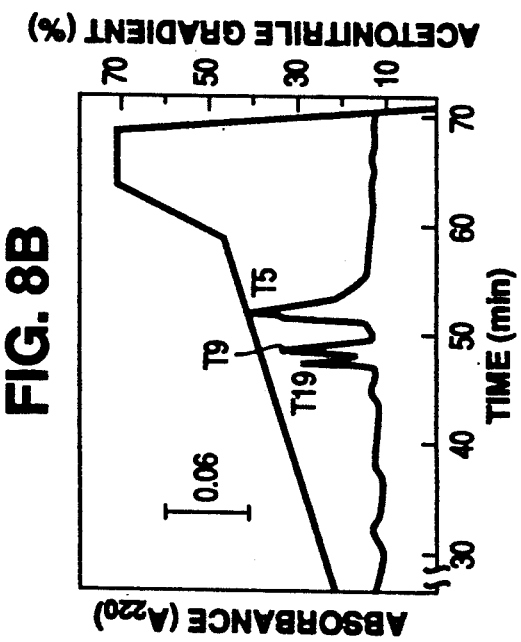
Figure 8D:
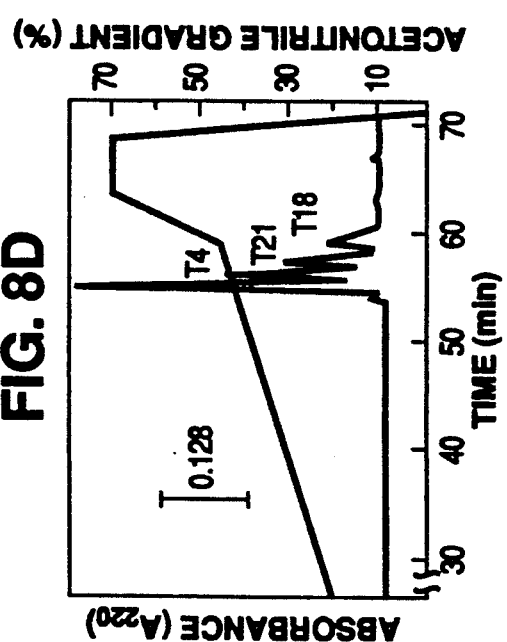

Non-homogenous peptides were rechromatographed under different conditions (examples are given in FIG. 8B-E); FIGS. 8B, 8D and 8E illustrate rechromatography of the material under peaks T19, T9, T5; T4, T21, T18; and T7, T13, respectively, of FIG. 8A. The samples were diluted three-fold with 0.1% trifluoracetic acid and loaded onto a Brownlee Spheri-5 RP-18 column (2.1×30 mm). The column was eluted with 0.1% trifluoracetic acid and a linear gradient of acetonitrile indicated. FIG. 8C shows rechromatography of the peptides under peak T12, T22 of FIG. 8A. The column used was the same as in FIG. 8A, but it was eluted with 0.15 M NaCl in Milli-Q water with a gradient of acetonitrile as indicated.

Single peptides were then subjected to N-terminal amino acid sequencing using a gas phase sequencer. (Applied Biosystems Protein Sequencer, model 470A, with an on line PTH-analyzer, model 120A). Sequence information from a total of tryptic peptides was obtained (FIG. 9). Additional sequence information was obtained by N-terminal sequencing of intact PD-ECGF, and by analysis of fragments obtained by digestion with CNBr of Staphylococcal V8 protease, using similar amounts of starting material.

In FIG. 9, tryptic fragments are indicated by (/...) and designations refer to peaks in FIG. 1. N-terminal sequence (/---), Staphylococcus protease V8 fragments (/+++) and a CNBr fragment (/===) of PD-ECGF are also indicated, as well as cysteine residues (*), a potential N-glycosylation site (#), and a possible site of polymorphism (@). Internal repeats are overlined.

Preparation of Antibodies to PD-ECGF

To aid in cloning of cDNA for PD-ECGF, a specific polyclonal antiserum against PD-ECGF was raised and used in immunoblotting to localize a source of production of PD-ECGF.

The antiserum was prepared by diluting pure PD-ECGF to a concentration of 20 ug/ml in 10 mM phosphate buffer, pH 7.4 with 150 mM NaCl. Then, ten micrograms of pure PD-ECGF was mixed with an equal volume of Freund's complete adjuvant and injected intramuscularly into a rabbit. The rabbit was boosted 2 weeks later with 10 ug of PD-ECGF in Freund's incomplete adjuvant. After that, the rabbit was boosted every 2-3 weeks with 5 ug of PD-ECGF in Freund's incomplete adjuvant. The immunoglobulin fraction was purified by applying 4 mL of immune serum to a 2-mL column of protein A-Sepharose (Pharmacia) equilibrated with 100 mM phosphate buffer, pH 7.4. The column was washed with the same buffer and then eluted with 50 mM citrate buffer, pH 3.0. The eluate from the column was rapidly neutralized with 1 M Tris-HCl, pH 7.4.

Since PD-ECGF occurs in platelets, several hematopoietic cell lines were tested, but none was found that synthesized PD-ECGF. A strong 45 kDa band was, however, found when an extract of a term human placenta was analyzed by immunoblotting. The human term placenta was minced and homogenized with 4 volumes of phosphate buffer saline (PBS). To the homogenate was added ammonium sulfate at 28% saturation; after centrifugation additional ammonium sulfate was added to the supernatant, to 42% saturation (1). The precipitate, recovered after centrifugation, was dissolved in PBS. Samples of 100 ng of PD-ECGF, purified from human platelets as described previously, and 375 ug of ammonium sulfate fractionated human placenta extract were subjected to SDS-gel electrophoresis in 10-18% gradient polyacrylamide gel under reducing conditions, and transferred to a nitrocellulose membrane in a buffer containing 20% ethanol, 150 mM glycine, and 20 mM Tris-HCl, pH 8.4, at 200 mA. The nitrocellulose membrane was incubated in 150 mM NaCl, 10 mM Tris-HCl, pH 7.4, 10% bovine serum albumin to block non-specific binding, incubated in a 1:50 dilution of a specific rabbit PD-ECGF antiserum, washed twice with 150 mM NaCl, 10 mM Tris-HCl, pH 7.4, and twice with 150 mM NaCl, 10 mM Tris-HCl, pH 7.4, 0.05% Triton X-100. The nitrocellulose membrane was then incubated with $^{125}$I-labeled Staphylococcal protein A ($5 \times 10^5$ cpm/ml), and washed as described above. Blots were subjected to autoradiography. PD-ECGF purified from platelets occurs as a doublet of about 45 kDa, probably due to proteolysis during preparation.

Figure 10:
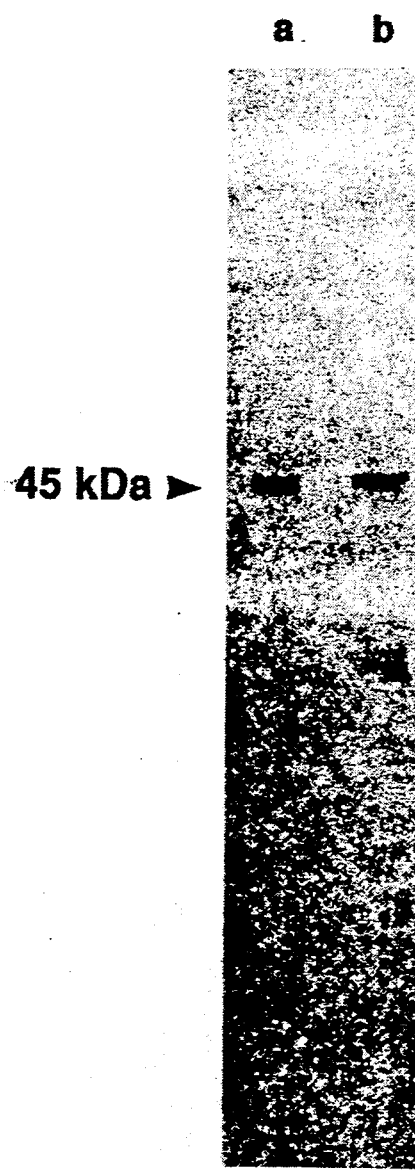
FIG. 10. Immunoblot analysis of a human placental extract.

FIG. 10 illustrates an immunoblot analysis of a human placenta extract (lane a) and PD-ECGF purified from human platelets (lane b) using the PD-ECGF polyclonal antiserum.

cDNA Cloning of PD-ECGF

A. Preparation of cDNA

A cDNA library was therefore constructed in λgt10 using poly(A)+RNA from human placenta.

Total RNA was isolated from a human placenta of 22 weeks of gestatum by the method of Han, et al. supra. Poly (A)+RNA was purified by chromatography on an oligo(dT) column. A cDNA library was constructed in λgt10 following the method described by Watson et al. in DNA Cloning Vol. 1 (ed. Glover, D.M.), pg. 179-88; (1985) with some modifications. For synthesis of the first strand, cloned murine leukemia virus reverse transcriptase (Bethesda Research Laboratory) was used. Following the first strand synthesis, oligo(dG) was added to its 3' end by terminal transferase. Second strand synthesis was primed by addition of an external primer of oligo(dC), as well as internal RNA primers made by RNaseH.

B. Selection of Oligonucleotides and Screening

The information from amino acid sequencing of peptides was used to select and synthesize five unique oligonucleotides. Five unique oligonucleotides were deduced from the amino acid sequence by the method of Lathe supra and prepared by an Applied Biosystems DNA synthesizer 381A. The oligonucleotide sequences were as follows:

228,
5'TGTGTGGGCCATGCCCTGGAGGTGGAGGAGGCCCTGCTGTGCATGGATGGCGCTGGCCCCCCTGACCTGCGG3'
231, 5'GTGGCTGCTGCCCTGACAGCCATGGACAAGCCCCTGGGCCGG3';
240,
5'GGCCTGGGCCACACAGGCGGCACCGGACAAGCTGGAGTCCATCCCTGGCTTCAATGTGATCCAGTCCCCTGAGCAGATGCAGGTGCTG3';
258,
5'GCCCCCCCTGCCCCTGAGGACTTCTCTGGCGAGGGCTCCCAGGGCCTGCCTGACCCC3';
259,
5'GTGGCTGCCCAGGGCGTGGACCCGGCCTGGCCCGGGCCCTGTGCTCTGGCTCCCCTGCTGAGCGGCGGCAGCTGCAGCC3'.

These oligonucleotide probes were labeled by end-tailing with a $^{32}$P-dCTP and deoxynucleotide terminal transferase or were used as templates to synthesize radiolabeled complementary strands by oligonucleotide primers, a $^{32}$P-dCTP and Klenow fragment.

The placenta library was screened with individual oligonucleotide probes. About three hundred thousand independent clones from the human placenta λgt10 cDNA library were plated and filter replicas were made using Hybond N nylon filters (Amersham). The filters were prehybridized in a solution of 20% formamide, 5×SSC (SSC=150 mM NaCl, 15 mM sodium citrate), 50 mM sodium phosphate, pH 6.8, 1 mM sodium pyrophosphate, 5×Denhardt's solution, 50 ug/ml denatured salmon sperm DNA and 100 uM ATP for 6 h at 42° C. Thereafter, labeled oligonucleotide probes were added to the solution and incubation prolonged for an additional 12-18 h. Filters were washed four times with 0.2×SSC in 0.1% sodium dodecylsulfate (SDS) for 20 min each time. Washing temperatures were varied from 37° C. to 42° C. according to the oligonucleotide length. Filters were exposed to Kodak X-Omat AR films with Dupont Cronex intensifier for 12-48 h.

Three out of three hundred thousand clones were positive with two of the five probes, probes 228 and 240.

C. Subcloned and Sequencing

The three clones, λPL5, λPL7 and λPL8, were isolated and the cDNA inserts were subclones. The original clones λPL5, λPL7 and λPL8, have inserts of about 1.7, 1.0 and 1.8 kb, respectively (Bluescript, Strategene). Restriction mapping showed that the inserts were colinear with each other (FIG. 4A). The restriction enzymes used were: B, BamHI; K, KpnI; S, SalI; and Sm, SmaI.

The inserts were also cloned into MI3mp18 for sequencing. The nucleotide sequencing strategy for the λPL8 insert, the longest insert, is also shown in FIG. 11A. Double stranded forms of M13 were subjected to sequential deletion using exonucleases III and VII following the method of Yanisch-Perron, et al. Gene 33: 103-119 (1985). Single-stranded DNAs were purified from each deletants and nucleotide sequences were determined by the dideoxy-terminatior method following Sanger et al., Proc. Natl. Acad. Sci. USA 74: 5463-5467 (1972). Sequences which were difficult to determine by this procedure were examined by the Maxam-Gilbert method (1980).

Nucleotide sequence of the λPL8 insert and deduced amino acid sequence of PD-ECGF is shown in FIG. 11B. The putative initiation codon is at nucleotides 124-126. An in-frame stop codon (nucleotides 28-30) upstream of the initiation codon is underlined, and a stop codon at nucleotides 1570-1572 is marked with an asterisk. The polyadenylation signal (nucleotides 1568–1573) is underlined with an arrow. Regions corresponding to the prepared oligonucleotide probes, 228, 231, 240, 258 and 259, are underlined with broken lines.

Sequence of PD-ECGF

Nucleotide sequencing of the λPL8 insert revealed a short GC-rich 5' untranslated region, an open reading frame predicting the translation of a 482 amino acid long protein ($M_r$ 49,971), and a short 3' untranslated sequence sequence containing a poly (A)+ tail (FIG. 11B). The translation is probably initiated at the ATG at nucleotides 124–126, since the surrounding nucleotide sequence follows the rules for translation initiation, whereas ATG at nucleotides 136–138 does not. Furthermore, there are no other ATGs between an in frame stop codon at nucleotides 28–30 and the nucleotides coding for the N-terminus of intact PD-ECGF (FIG. 9). A stop codon (TAA) is present at nucleotides 1570–1572. This stop codon is part of the polyadenylation signal (nucleotides 1568–1573). Fourteen nucleotides down-stream of this signal, a long stretch of poly(A)+ was found. A similar overlap of the stop codon and the polyadenylation signal has been reported for human choriogonadotropin B-chain.

Out of the 482 amino acids of PD-ECGF deduced from the cDNA clone, 389 were identified by amino acid sequencing (FIG. 9). The N-terminal sequence of PD-ECGF starts 10 amino acids downstream of the proposed translation initiation site, indicating that the molecule undergoes limited proteolytic processing after synthesis. The C-terminal amino acids predicted from the cDNA sequence, except the last four, were identified by amino acid sequencing. It is not known whether PD-ECGF undergo proteolytic processing in the C-terminus. If so, a maximum of four amino acids are removed. The $M_r$ of the mature protein would thus be 48,600–49,000, in reasonable agreement with the estimate of 45,000 obtained from SDS-gel electrophoresis of pure PD-ECGF.

The predicted amino acid sequence from the cDNA clone matched perfectly the previously obtained amino acid sequence in all positions, except in position 471, where the nucleotide sequence predicts a leucine residue, whereas a serine residue was found in both of two different peptides obtained from this region (FIG. 9). It is possible that polymorphism occurs at this position.

Matching the sequence of PD-ECGF with those of the PIR, EMBL and Genbank databases (releases 15, 14 and 56, respectively) revealed no striking homologies to other proteins. Short internal repeats in the sequence were noted (overlined in FIG. 2). One important feature of the sequence is the lack of a hydrophobic signal sequence suggesting that PD-ECGF is not a classical secretory protein. The sequence contains only one tyrosine residue, which probably is not exposed on the surface of the molecule, since attempts to radiolabel PD-ECGF with $^{125}$I using the chloramine T method, resulted in a very low incorporation of radioactivity. There is one potential N-glycosylation site, Asn-63 (FIG. 9). The PTH-amino acid yield of the corresponding tryptic peptide decreased dramatically, just before this residue (FIG. 9). This could be due to the formation of a cyclic compound of the asparagine residue and the following glycine residue, which can occur only if the aspargine residue is nonglycosylated. This, in combination with the $M_r$ of PD-ECGF as determined by SDS-gel electrophoresis, compared with the $M_r$ predicted from the cDNA clone, suggest that Asn-63 is not glycosylated. There are a total of 7 cysteine residues, indicating that the molecule contains at least one free SH group.

Southern and Northern Blotting

Figure 12A:
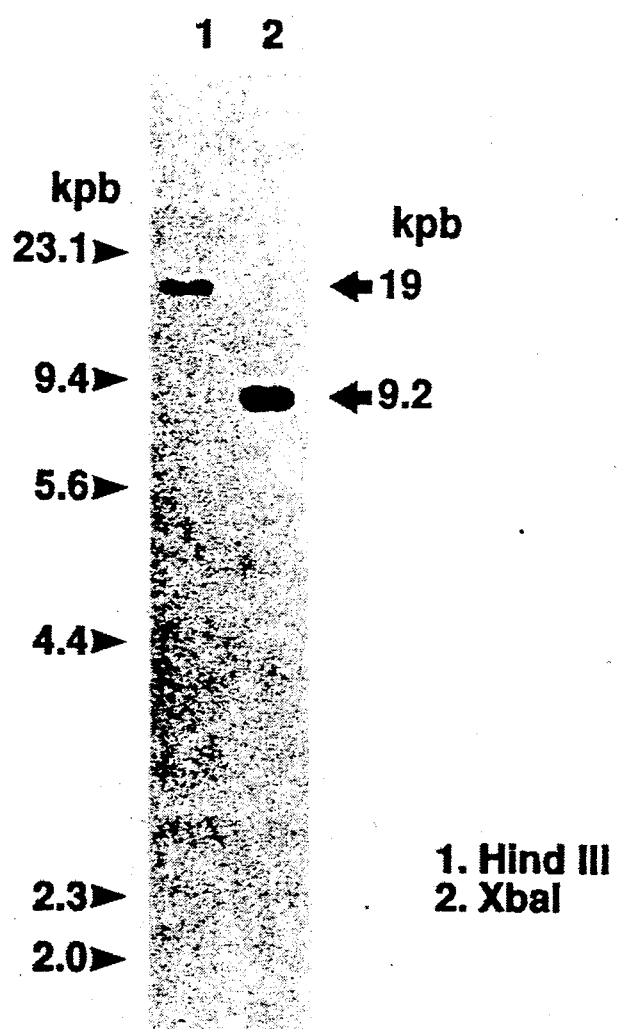
FIG. 12A-B. A) Southern blot analysis of human DNA. B) Northern blot analysis of placental RNA.

To obtain information about the genomic structure of the human PD-ECGF gene, Southern blotting analysis of human DNA was performed using the insert of pPL8 as a probe. High-molecular-weight human genomic DNA was prepared from normal human leukocytes. Samples were digested by restriction enzymes, subjected to electrophoresis in agar and blotted to nitrocellulose membranes (Schleicher and Schull). As shown in FIG. 12A, ten ug of human placenta DNA was cut with HindIII (lane 1) or XbaI (lane 2), and then subjected to electrophoresis in agar and hydridized by a PD-ECGF cDNA probe from the pPL8 insert. Single bands of 19 kb and 9.2 kb was observed after digestions with HindIII and XbaI, respectively. This suggests that only one copy of the PD-ECGF gene is present in the human genome. Indeed, analysis of human genomic PD-ECGF clones supports this conclusion.

Human placenta poly(A)+RNA was examined by Northern blotting using the pPL5 insert as a probe. Poly(A)+RNA was purified from 22-weeks-gestation human placenta as described above. One ug of RNA was electrophoresed in a 0.9% formalin denaturing gel and blotted to Hybond N nylon filter (Amersham). Hybridization was preformed in a solution of 50% formamide, 0.65 M NaCl, 0.1 M sodium Pipes, pH 6.8, 10% dextran sulgate, 5×Denhardt's solution, 0.1% SDS, 5 mM EDTA and 100 ug/ml salmon sperm DNA at 42° for 18 h, and then washed four times with 2×SSC, 0.2% sodium phosphate, 0.1% SDS for 20 min. periods at 50° C.

Figure 12B:
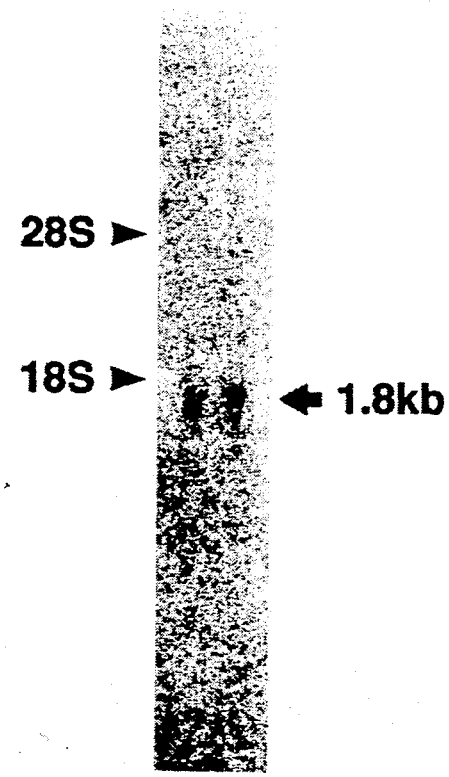

A single transcript of about 1.8 kb was observed (FIG. 12B). Since the longest cDNA clone found, λPL8, has an insert of about 1.8 kb, it most likely represents a full-length copy of the PD-ECGF transcript.

Expression of PD-ECGF cDNA

In order to verify the authenticity of the cDNA clone and to provide a replicable expression vector carrying the PD-ECGF gene, it was expressed in NIH3T3 cells. The pPL8 insert was subcloned into the pLJ expression vector to give pLPL8J. This vector has Molone leukemia virus LTR as a promoter to drive the cDNA transcription, as well as a neomycin resistance gene as a selection marker. The pLPL8J and pLJ constructs were introduced in the NIH3T3 cells by the calcium phosphate co-precipitation method, and cell lines were selected by neomycin.

NIH3T3 cells transfected with pLJ or with pLPL8J were grown to confluence in 10 cm cell culture dishes in Dulbecco's modified Eagles's medium (DMEM) supplemented with 10% calf serum and antibiotices. The cells were then cultured for 24 h in serum-free consitions in DMEM supplemented with 1% bovine serum albumin, 7.8 ug/ml cholesterol, 5.5 ug/ml oleic acid, 8 ug/ml L-a-phosphatidylcholine and 0.2 mg/ml transferin. After collecting the conditioned media, the cells were washed twice in PBS and then scraped into 1 ml of PBS. Following careful resuspension, a cell lysate was prepared by disrupting the cells by three cycles of freezing and thawing, followed by centrifugation at 25,000 g for 30 min. and collection of the supernatants. For the preparation of cell lysates, the cells were washed and resuspended in PBS containing 1 mM phenylmethylsulfonyl fluoride (Sigma), 150 KIU aprotinin (Sigma) and 10 mM EDTA. Growth-promoting activity was measured by the incorporation of $^3$H-thymidine into porcine aortic endothelial cells in the absence or presence of 2 ug/ml of PD-ECGF antibody purified by protein A-Sepharose. Immunoblotting was performed as described.

Figure 13C:
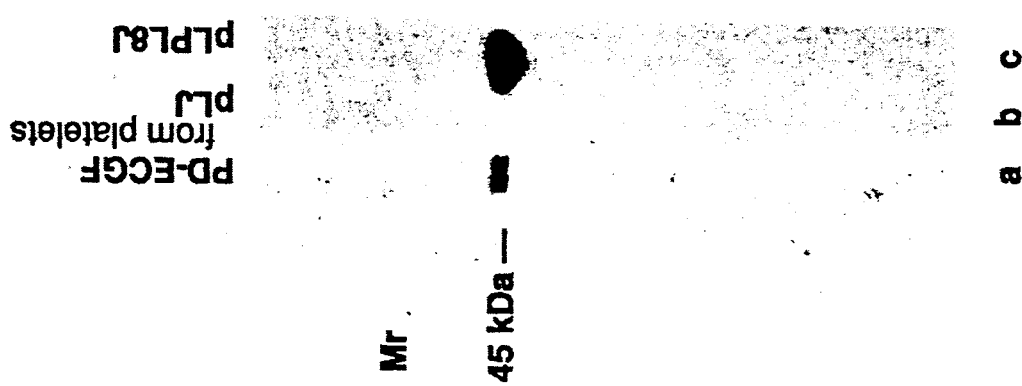
FIG. 13A–C. A and B) Biosynthesis of recombinant PD-ECGF in NIH3T3 cells. C) Immunoblot analysis of NIH3T3 cells expressing recombinant PD-ECGF.
Figure 13A:
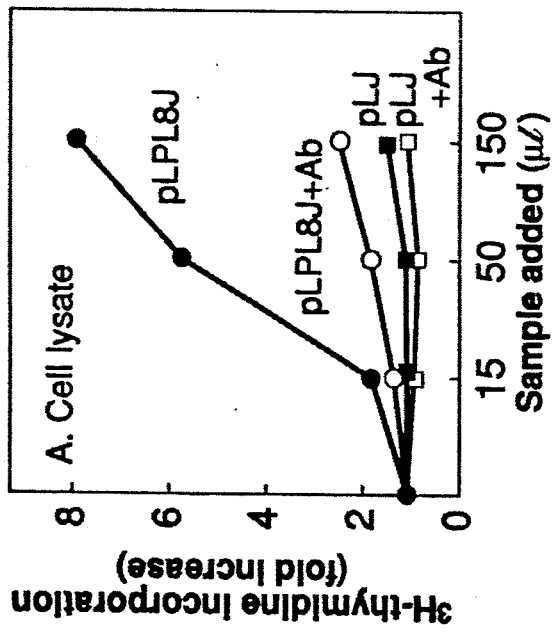
Figure 13B:

Analysis of cell lysate and conditioned medium of one cell line transfected with pLPL8J, revealed growth promoting activity for porcine aortic endothelial cells in the cell lysate, but not in the conditioned medium (FIG. 13A,B). The activity was completely neutralized by a specific rabbit antiserum against PD-ECGF, indicating that the activity was due to the synthesis of functionally active PD-ECGF by the cell in (FIG. 13A). The NIH3T3 cell line transfected with pLJ did not contain any growth promoting activity for porcine aortic endothelial cells. The cell lysate of the cell line transfected with pLPL8J was furthermore found to contain a 45 kDa component in immunoblotting experiments using the antiserum against PD-ECGF (FIG. 13C). The size of the product was similar to that of human PD-ECGF purified from platelets (FIG. 13C). These data show that the purified, sequenced and cloned PD-ECGF molecule is responsible for the observed biological effect on porcine endothelial cells. These data additionally showed that recombinant PD-ECGF can be expressed in cultured cells.

Chemotactic Responses to PD-ECGF

The effect of PD-ECGF on the migration of bovine aortic endothelial cells (BAEC) and smooth muscle cells (SMC) was determined.

Chemotaxis assays of BAEC and SMC were performed in 48-well micro chambers. Gelatin and fibronectin coating of the Nucleopore filters was necessary for BAEC adhesion. Cells (18,000 BAEC, 25,000 SMC per well) were added to the upper wells. Serum-free Dulbecco's modified Eagle's medium (DMEM) was used for SMC migration, DMEM was supplemented with 1% FBS for BAEC migration. The number of cells which had migrated during a 5 h incubation period to the lower surface of the filter were counted in three high power fields. All experiments were done in triplicate. In FIG. 14A, the Dose dependent migration of BAEC is indicated by closed circles and on left ordinate and similarly for SMC by open circles and on right ordinate. Controls are shown as a histogram I) BAEC medium only, II) BAEC medium plus 10ng/ml basic FGF, III) SMC medium only, IV) SMC medium plus 5% FCS.

FIG. 14a shows the dose-dependent effect of PD-ECGF on the migration of bovine aortic endothelial cells (BAECs), which at saturation (5-10 ng/ml) is comparable to the potency of basic FGF as a chemotactic factor. Half-maximal stimulation occurred at a concentration of about 1 ng/ml. Consistent with its mitogenic target cell specificity for endothelial cells PD-ECGF did not induce smooth muscle cell migration under assay conditions. Controls using serum and platelet-derived growth factor induced extensive smooth muscle cell migration in the same experiment.

Checkerboard analysis revealed that BAEC migration induced by PD-ECGF is due to directed cell migration (chemotaxis) and not random migration (chemokinesis). The data are shown in FIG. 14B and represent % cell number per field. Standard deviations were below 15%. The values on the diagonal indicate chemokinetic migration and the values below the diagonal indicate chemotaxis.

Finally, antibodies which neutralize the mitogenic activity of PD-ECGF in vitro also neutralized the chemotactic activity (FIG. 14C) indicating that PD-ECGF is responsible for this activity.

The inhibition of BAEC migration using PD-ECGF antibodies was performed as described above and the examples shown in FIG. 14C are 1) Control, 2) 5ng/ml pure PD-ECGF, and 3) 5ng/ml pure PD-ECGF plus 300 ng/ml anti PD-ECGF antibodies.

Angiogenic Properties of PD-ECGF

The effect of PD-ECGF in vivo was tested on the developing vascular system of the chick chorioallantoic membrane (CAM). Test substances were incorporated into methylcellulose disks (10ul) and transplanted onto a 9 day old CAM as described by Risau, et al. Proc. Natl. Acad. Sci. USA 83: 3855-3859 (1986). CAMS were analyzed daily for two days. Disks are visible by their light reflections. FIG. 15 shows the induction of Angiogenesis on the chick chorioallantoic membrane by a) partially purified PD-ECGF (purified through the hydroxylapatite step, 1% pure, 1.2 mg of protein/ml; 5 ul per methylcellulose disk), b) 50 ng pure PD-ECGF, and c) partially purified PD-ECGF (as in a) incubated for 20 min with anti-PD-ECGF antiserum (2.5 ul of each solution) (magnification × 10).

Figure 15A:
FIG. 15A–C. A and B) Induction of angiogenesis by PD-ECGF on the chick chorioallantoic membrane. C) Inhibition of induction of angiogenesis by antibodies that react with PD-ECGF.
Figure 15B:
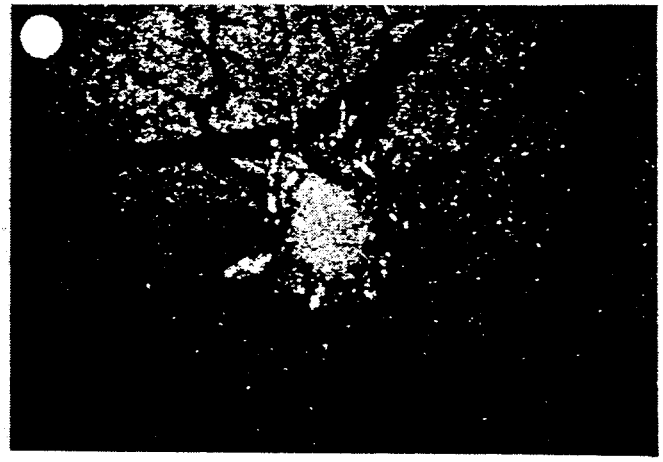
Figure 15C:

Partially purified PD-ECGF consistently induced a strong angiogenic response (FIG. 15A). Furthermore, pure PD-ECGF at a dose of 50 ng induced angiogenesis in the CAM (FIG. 15B). These results are summarized in Table 3. Antibodies against PD-ECGF greatly inhibited PD-ECGF induced angiogenesis in this assay (FIG. 15C). Thus, the angiogenic response is unlikely to be due to inflammation or other factors than PD-ECGF present in the preparation.

TABLE 3

| Angiogenic Properties of PD-ECGF on the CAM | | | |
|---|---|---|---|
| | ANGIOGENIC REACTION | | |
| TRANSPLANT | ++ | + | − |
| Partially purified PD-ECGF (2.5-5 ul/disk) | 54 | 4 | 7 |
| Partially purified PD-ECGF (2.5 ul/disk) plus anti-PD-ECGF serum (2.5 ul/disk) | 7 | 2 | 13 |
| Pure PD-ECGF (50 ng/disk) | 11 | 3 | 1 |

Figure 16A:
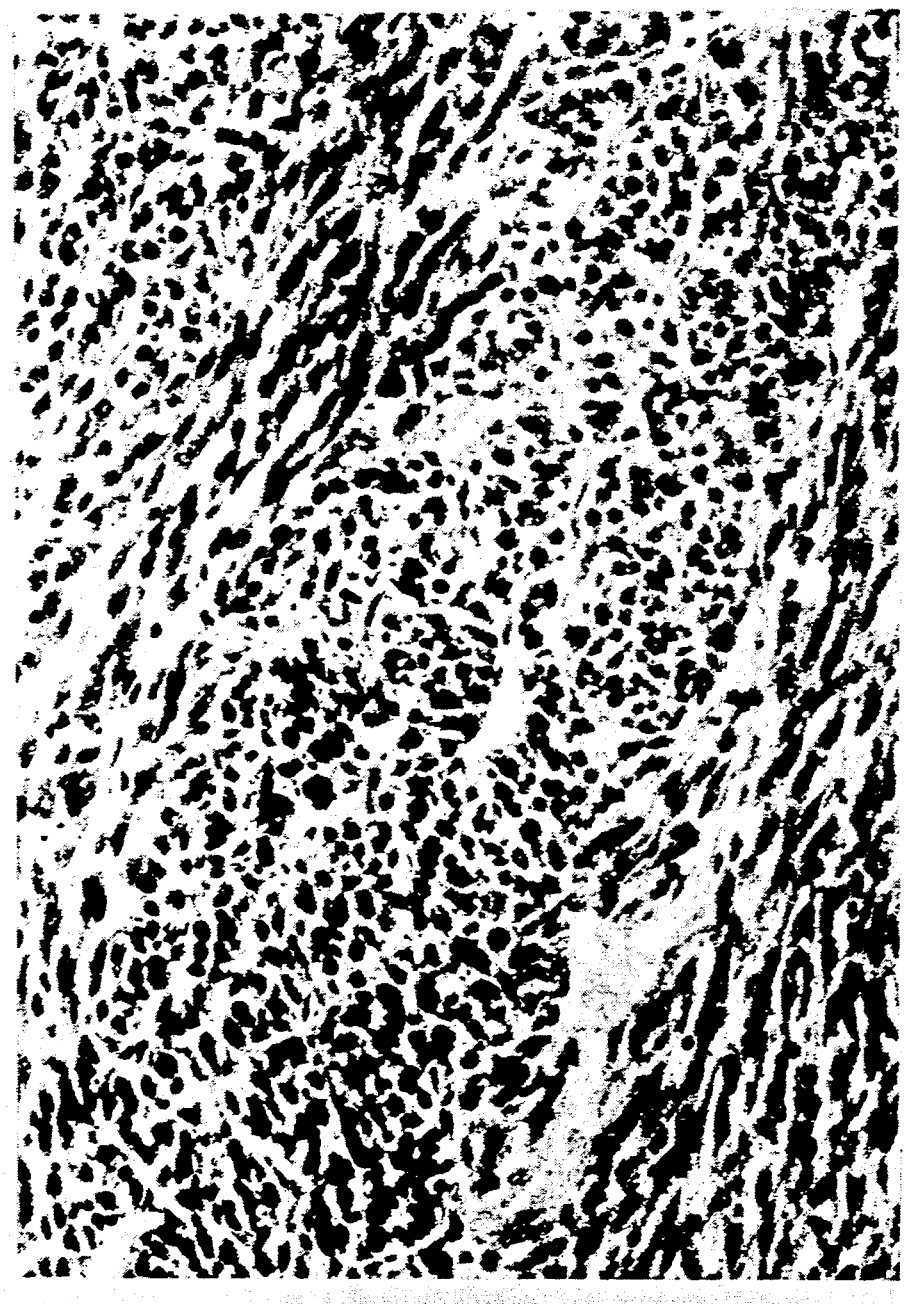
FIG. 16. A and B) Induction of angiogenesis in mouse a1-1 tumors transfected with cDNA clones expressing recombinant PD-ECGF.
Figure 16B:
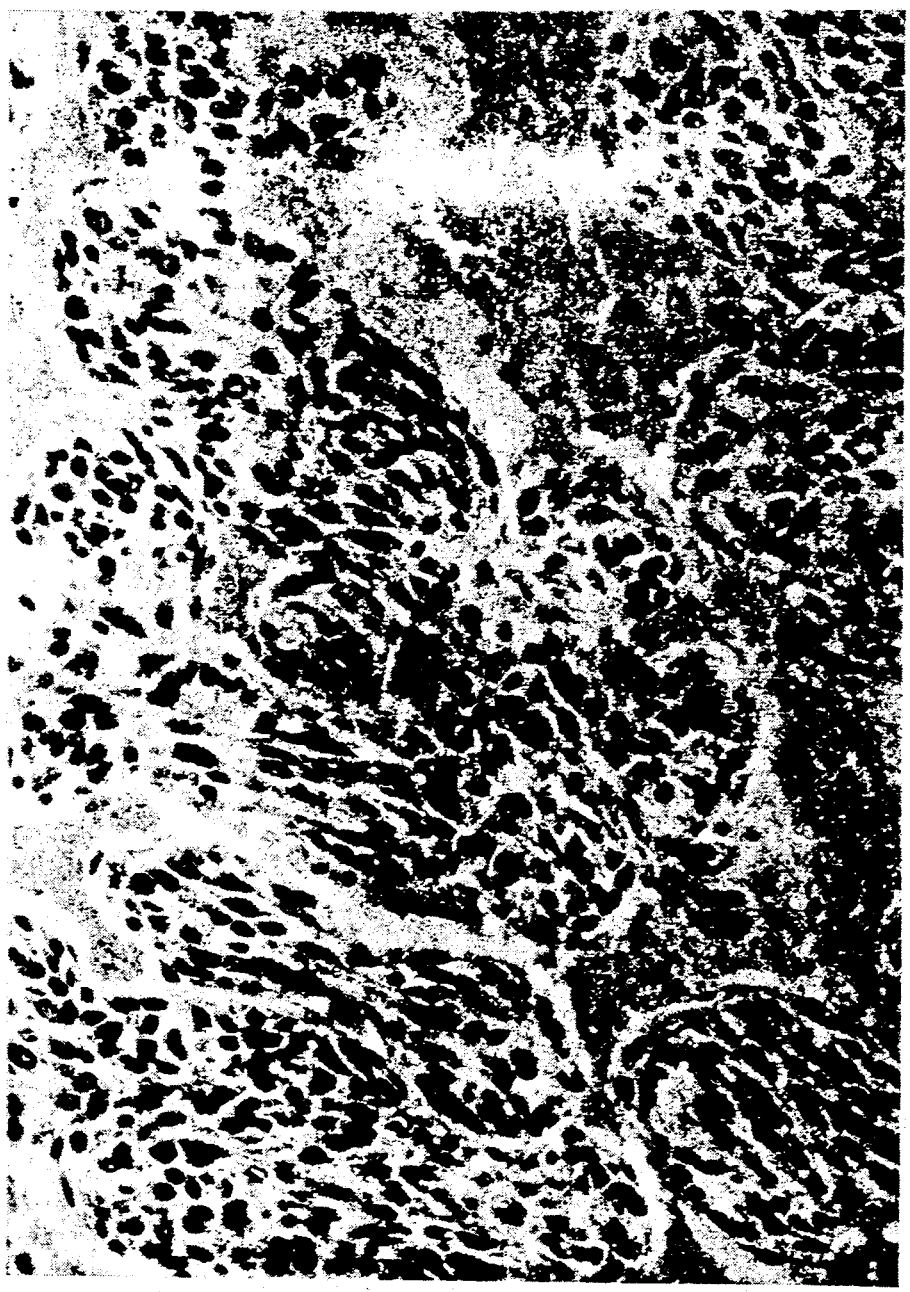

Number of samples is indicated in each column.
++: Strong angiogenic reaction
+: Less pronounced angiogenic reaction, in some cases only few vessels converging to the transplant
−: Unaffected vascular pattern To investigate the in vivo effects of PD-ECGF, pLPL8J and pLJ without insert were transfected by electroporation into al-1 cells. al-1 is a NIH 3T3 cell transformed by human activated H-ras and is tumorigenic in nude mice. After transfected al-1 cells were selected by G418 resistance, they were injected into nude mice subcutaneously. In two weeks, tumors grew to be about 2 cm in diameter and they were harvested and fixed in formaldehyde. Histological examination (FIG. 16) revealed that tumors developed from al-1 transfected with pLPL8J have marked blood vessels in contrast with the few vessels in tumors from al-1 transfected with pLJ without cDNA inserts. This observation indicates that human PD-ECGF is angiogenic in mice.

What is claimed:

1. Isolated nucleic acid molecule which encodes platelet derived endothelial cell growth factor (PD-ECGF) which has a molecular weight of 45 kilodaltons, is angiogenic and chemotactic, does not bind to heparin and does not stimulate proliferation of fibroblasts.

2. Isolated nucleic acid molecule of claim 1, encoding platelet derived endothelial cell growth factor having amino acid sequence:

| | | | | | | | | | | | | | | |
|---|---|---|---|---|---|---|---|---|---|---|---|---|---|---|
| Ala | Pro | Pro | Ala | Pro | Gly | Asp | Phe | Ser | Gly | Glu | Gly | Ser | Gln | Gly |
| Leu | Pro | Asp | Pro | Ser | Pro | Glu | Pro | Lys | Gln | Leu | Pro | Glu | Leu | Ile |
| Arg | Met | Lys | Arg | Asp | Gly | Gly | Arg | Leu | Ser | Glu | Ala | Asp | Ile | Arg |
| Gly | Phe | Val | Ala | Ala | Val | Val | Asn | Gly | Ser | Ala | Gln | Gly | Ala | Gln |
| Ile | Gly | Ala | Met | Leu | Met | Ala | Ile | Arg | Leu | Arg | Gly | Met | Asp | Leu |
| Glu | Glu | Thr | Ser | Val | Leu | Thr | Gln | Ala | Leu | Ala | Gln | Ser | Gly | Gln |
| Gln | Leu | Glu | Trp | Pro | Glu | Ala | Trp | Arg | Gln | Gln | Leu | Val | Asp | Lys |
| His | Ser | Thr | Gly | Gly | Val | Gly | Asp | Lys | Val | Ser | Leu | Val | Leu | Ala |
| Pro | Ala | Leu | Ala | Ala | Cys | Gly | Cys | Lys | Val | Pro | Met | Ile | Ser | Gly |
| Arg | Gly | Leu | Gly | His | Thr | Gly | Gly | Thr | Leu | Asp | Lys | Leu | Glu | Ser |
| Ile | Pro | Gly | Phe | Asn | Val | Ile | Gln | Ser | Pro | Glu | Gln | Met | Gln | Val |
| Leu | Leu | Asp | Gln | Ala | Gly | Cys | Cys | Ile | Val | Gly | Gln | Ser | Glu | Gln |
| Leu | Val | Pro | Ala | Asp | Gly | Ile | Leu | Tyr | Ala | Ala | Arg | Asp | Val | Thr |
| Ala | Thr | Val | Asp | Ser | Leu | Pro | Leu | Ile | Thr | Ala | Ser | Ile | Leu | Ser |
| Lys | Lys | Leu | Val | Glu | Gly | Leu | Ser | Ala | Leu | Val | Val | Asp | Val | Lys |
| Phe | Gly | Gly | Ala | Ala | Val | Phe | Pro | Asn | Gln | Glu | Gln | Ala | Arg | Glu |
| Leu | Ala | Lys | Thr | Leu | Val | Gly | Val | Gly | Ala | Ser | Leu | Gly | Leu | Arg |
| Val | Ala | Ala | Ala | Leu | Thr | Ala | Met | Asp | Lys | Pro | Leu | Gly | Arg | Cys |
| Val | Gly | His | Ala | Leu | Glu | Val | Glu | Glu | Ala | Leu | Leu | Cys | Met | Asp |
| Gly | Ala | Gly | Pro | Pro | Asp | Leu | Arg | Asp | Leu | Val | Thr | Thr | Leu | Gly |
| Gly | Ala | Leu | Leu | Trp | Leu | Ser | Gly | His | Ala | Gly | Thr | Gln | Ala | Gln |
| Gly | Ala | Ala | Arg | Val | Ala | Ala | Leu | Asp | Asp | Gly | Ser | Ala | Leu | |
| Gly | Arg | Phe | Glu | Arg | Met | Leu | Ala | Ala | Gln | Gly | Val | Asp | Pro | Gly |
| Leu | Ala | Arg | Ala | Leu | Cys | Ser | Gly | Ser | Pro | Ala | Glu | Arg | Arg | Gln |
| Leu | Leu | Pro | Arg | Ala | Arg | Glu | Gln | Glu | Glu | Leu | Leu | Ala | Pro | Ala |
| Asp | Gly | Thr | Val | Glu | Leu | Val | Arg | Ala | Leu | Pro | Leu | Ala | Leu | Val |
| Leu | His | Glu | Leu | Gly | Ala | Gly | Arg | Ser | Arg | Ala | Gly | Glu | Pro | Leu |
| Arg | Leu | Gly | Val | Gly | Ala | Glu | Leu | Leu | Val | Asp | Val | Gly | Gln | Arg |
| Leu | Arg | Arg | Gly | Thr | Pro | Trp | Leu | Arg | Val | His | Arg | Asp | Gly | Pro |
| Ala | Leu | Ser | Gly | Pro | Gln | Ser | Arg | Ala | Leu | Gln | Glu | Ala | Leu | Val |
| Leu | Ser | Asp | Arg | Ala | Pro | Phe | Ala | Ala | Pro | Leu | Pro | Phe | Ala | Glu |
| Leu | Val | Leu | Pro | Pro | Gln | Gln | | | | | | | | |

3. Isolated nucleic acid molecule of claim 1, encoding platelet derived endothelial cell growth factor having amino acid sequence:

| | | | | | | | | | | | | | | |
|---|---|---|---|---|---|---|---|---|---|---|---|---|---|---|
| | | | | | Met | Ala | Ala | Leu | Met | Thr | Pro | Gly | Thr | Gly |
| Ala | Pro | Pro | Ala | Pro | Gly | Asp | Phe | Ser | Gly | Glu | Gly | Ser | Gln | Gly |
| Leu | Pro | Asp | Pro | Ser | Pro | Glu | Pro | Lys | Gln | Leu | Pro | Glu | Leu | Ile |
| Arg | Met | Lys | Arg | Asp | Gly | Gly | Arg | Leu | Ser | Glu | Ala | Asp | Ile | Arg |
| Gly | Phe | Val | Ala | Ala | Val | Val | Asn | Gly | Ser | Ala | Gln | Gly | Ala | Gln |
| Ile | Gly | Ala | Met | Leu | Met | Ala | Ile | Arg | Leu | Arg | Gly | Met | Asp | Leu |
| Glu | Glu | Thr | Ser | Val | Leu | Thr | Gln | Ala | Leu | Ala | Gln | Ser | Gly | Gln |
| Gln | Leu | Glu | Trp | Pro | Glu | Ala | Trp | Arg | Gln | Gln | Leu | Val | Asp | Lys |
| His | Ser | Thr | Gly | Gly | Val | Gly | Asp | Lys | Val | Ser | Leu | Val | Leu | Ala |
| Pro | Ala | Leu | Ala | Ala | Cys | Gly | Cys | Lys | Val | Pro | Met | Ile | Ser | Gly |
| Arg | Gly | Leu | Gly | His | Thr | Gly | Gly | Thr | Leu | Asp | Lys | Leu | Glu | Ser |
| Ile | Pro | Gly | Phe | Asn | Val | Ile | Gln | Ser | Pro | Glu | Gln | Met | Gln | Val |
| Leu | Leu | Asp | Gln | Ala | Gly | Cys | Cys | Ile | Val | Gly | Gln | Ser | Glu | Gln |
| Leu | Val | Pro | Ala | Asp | Gly | Ile | Leu | Tyr | Ala | Ala | Arg | Asp | Val | Thr |
| Ala | Thr | Val | Asp | Ser | Leu | Pro | Leu | Ile | Thr | Ala | Ser | Ile | Leu | Ser |
| Lys | Lys | Leu | Val | Glu | Gly | Leu | Ser | Ala | Leu | Val | Val | Asp | Val | Lys |
| Phe | Gly | Gly | Ala | Ala | Val | Phe | Pro | Asn | Gln | Glu | Gln | Ala | Arg | Glu |
| Leu | Ala | Lys | Thr | Leu | Val | Gly | Val | Gly | Ala | Ser | Leu | Gly | Leu | Arg |
| Val | Ala | Ala | Ala | Leu | Thr | Ala | Met | Asp | Lys | Pro | Leu | Gly | Arg | Cys |
| Val | Gly | His | Ala | Leu | Glu | Val | Glu | Glu | Ala | Leu | Leu | Cys | Met | Asp |
| Gly | Ala | Gly | Pro | Pro | Asp | Leu | Arg | Asp | Leu | Val | Thr | Thr | Leu | Gly |
| Gly | Ala | Leu | Leu | Trp | Leu | Ser | Gly | His | Ala | Gly | Thr | Gln | Ala | Gln |
| Gly | Ala | Ala | Arg | Val | Ala | Ala | Leu | Asp | Asp | Gly | Ser | Ala | Leu | |
| Gly | Arg | Phe | Glu | Arg | Met | Leu | Ala | Ala | Gln | Gly | Val | Asp | Pro | Gly |
| Leu | Ala | Arg | Ala | Leu | Cys | Ser | Gly | Ser | Pro | Ala | Glu | Arg | Arg | Gln |
| Leu | Leu | Pro | Arg | Ala | Arg | Glu | Gln | Glu | Glu | Leu | Leu | Ala | Pro | Ala |
| Asp | Gly | Thr | Val | Glu | Leu | Val | Arg | Ala | Leu | Pro | Leu | Ala | Leu | Val |
| Leu | His | Glu | Leu | Gly | Ala | Gly | Arg | Ser | Arg | Ala | Gly | Glu | Pro | Leu |
| Arg | Leu | Gly | Val | Gly | Ala | Glu | Leu | Leu | Val | Asp | Val | Gly | Gln | Arg |
| Leu | Arg | Arg | Gly | Thr | Pro | Trp | Leu | Arg | Val | His | Arg | Asp | Gly | Pro |
| Ala | Leu | Ser | Gly | Pro | Gln | Ser | Arg | Ala | Leu | Gln | Glu | Ala | Leu | Val |
| Leu | Ser | Asp | Arg | Ala | Pro | Phe | Ala | Ala | Pro | Leu | Pro | Phe | Ala | Glu |
| Leu | Val | Leu | Pro | Pro | Gln | Gln | | | | | | | | |

4. Isolated nucleic acid molecule of claim 1, encoding platelet derived endothelial cell growth factor and consisting of nucleotide sequence:

| | | | | | | | | | | | | | | |
|---|---|---|---|---|---|---|---|---|---|---|---|---|---|---|
GGGCAGTGGA CCGCTGTGCG CGAACCCTGA ACCCTACGGT 40
CCCGACCCGC GGGCGAGGCC GGGTACCTGG GCTGGGATCC 80
GGAGCAAGCG GGCGAGGGCA GCGCCCTAAG CAGGCCCGGA 120
GCG ATG GCA GCC TTG ATG ACC CCG GGA ACC GGG 153
GCC CCA CCC GCG CCT GGT GAC TTC TCC GGG GAA 186
GGG AGC CAG GGA CTT CCC GAC CCT TCG CCA GAG 219
CCC AAG CAG CTC CCG GAG CTG ATC CGC ATG AAG 252
CGA GAC GGA GGC CGC CTG AGC GAA GCG GAC ATC 285
AGG GGC TTC GTG GCC GCT GTG GTG AAT GGG AGC 318
GCG CAG GGC GCA CAG ATC GGG GCC ATG CTG ATG 351
GCC ATC CGA CTT CGG GGC ATG GAT CTG GAG GAG 384
ACC TCG GTG CTG ACC CAG GCC CTG GCT CAG TCG 417
GGA CAG CAG CTG GAG TGG CCA GAG GCC TGG CGC 450
CAG CAG CTT GTG GAC AAG CAT TCC ACA GGG GGT 483
GTG GGT GAC AAG GTC AGC CTG GTC CTC GCA CCT 516
GCC CTG GCG GCA TGT GGC TGC AAG GTG CCA ATG 549
ATC AGC GGA CGT GGT CTG GGG CAC ACA GGA GGC 582
ACC TTG GAT AAG CTG GAG TCT ATT CCT GGA TTC 615
AAT GTC ATC CAG AGC CCA GAG CAG ATG CAA GTG 648
CTG CTG GAC CAG GCG GGC TGC TGT ATC GTG GGT 681
CAG AGT GAG CAG CTG GTT CCT GCG GAC GGA ATC 714
CTA TAT GCA GCC AGA GAT TGT ACA GCC ACC GTG 747
GAC AGC CTG CCA CTC ATC ACA GCC TCC ATT CTC 780
AGT AAG AAA CTC GTG GAG GGG CTG TCC GCT CTG 813
GTG GTG GAC GTT AAG TTC GGA GGG GCC GCC GTC 846
TTC CCC AAC CAG GAG CAG GCC CGG GAG CTG GCA 879
AAG ACG CTG GTT GGC GTG GGA GCC AGC CTA GGG 912
CTT CGG GTC GCG GCA GCG CTG ACC GCC ATG GAC 945
AAG CCC CTG GGT CGC TGC GTG GGC CAC GCC CTG 978
GAG GTG GAG GAG GCG CTG CTC TGC ATG GAC GGC 1011
GCA GGC CCG CCA GAC TTA AGG GAC CTG GTC ACC 1044
ACG CTC GGG GGC GCC CTG CTC TGG CTC AGC GGA 1077
CAC GCG GGG ACT CAG GCC CAG GGC GCT GCC CGG 1110
GTG GCC GCG CTG GAC GAC GGC TCG GCC CTT 1143
GGC CGC TTC GAG CGG ATG CTG GCG GCG CAG GGC 1176
GTG GAT CCC GGT CTG GCC CGA GCC CTG TGC TCG 1209
GGA AGT CCC GCA GAA CGC CGG CAG CTG CTG CCT 1242
CGC GCC CGG GAG CAG GAG GAG CTG CTG GCG CCC 1275
GCA GAT GGC ACC GTG GAG CTG GTC CGG GCG CTG 1308
CCG CTG GCG CTG GTG CTG CAC GAG CTC GGG GCC 1341
GGG CGC AGC CGC GCT GGG GAG CCG CTC CGC CTG 1374
GGG GTG GGC GCA GAG CTG CTG GTC GAC GTG GGT 1407
CAG AGG CTG CGC CGT GGG ACC CCC TGG CTC CGC 1440
GTG CAC CGG GAC GGC CCC GCG CTC AGC GGC CCG 1473
CAG AGC CGC GCC CTG CAG GAG GCG CTC GTA CTC 1506
TCC GAC CGC GCG CCA TTC GCC GCC CCC TTG CCC 1539
TTC GCA GAG CTC GTT CTG CCG CCG CAG CAA TAA 1572
AGC TCC TTT GCC GCG AAA AAA AAA A 1597

5. A replicable expression vector comprising a promoter operably linked to the nucleic acid molecule of claim 1 which encodes platelet derived, endothelial cell growth factor.

6. The replicable expression vector of claim 5, further comprising a gene which confers resistance to an antibiotic.

7. A host cell transformed with the replicable expression vector of claim 5 which encodes platelet derived endothelial cell growth factor.

8. The transformed host cell of claim 7, wherein said host cell is NIH3T3.

9. The transformed host cell of claim 7, wherein said host cell is Escherichia coli.

10. The transformed host cell of claim 7, wherein said replicable expression vector encodes platelet derived endothelial cell growth factor having amino acid sequence:

| Ala | Pro | Pro | Ala | Pro | Gly | Asp | Phe | Ser | Gly | Glu | Gly | Ser | Gln | Gly |
|---|---|---|---|---|---|---|---|---|---|---|---|---|---|---|
| Leu | Pro | Asp | Pro | Ser | Pro | Glu | Pro | Lys | Gln | Leu | Pro | Glu | Leu | Ile |
| Arg | Met | Lys | Arg | Asp | Gly | Gly | Arg | Leu | Ser | Glu | Ala | Asp | Ile | Arg |
| Gly | Phe | Val | Ala | Ala | Val | Val | Asn | Gly | Ser | Ala | Gln | Gly | Ala | Gln |
| Ile | Gly | Ala | Met | Leu | Met | Ala | Ile | Arg | Leu | Arg | Gly | Met | Asp | Leu |
| Glu | Glu | Thr | Ser | Val | Leu | Thr | Gln | Ala | Leu | Ala | Gln | Ser | Gly | Gln |
| Gln | Leu | Glu | Trp | Pro | Glu | Ala | Trp | Arg | Gln | Gln | Leu | Val | Asp | Lys |
| His | Ser | Thr | Gly | Gly | Val | Gly | Asp | Lys | Val | Ser | Leu | Val | Leu | Ala |
| Pro | Ala | Leu | Ala | Ala | Cys | Gly | Cys | Lys | Val | Pro | Met | Ile | Ser | Gly |
| Arg | Gly | Leu | Gly | His | Thr | Gly | Gly | Thr | Leu | Asp | Lys | Leu | Glu | Ser |
| Ile | Pro | Gly | Phe | Asn | Val | Ile | Gln | Ser | Pro | Glu | Gln | Met | Gln | Val |
| Leu | Leu | Asp | Gln | Ala | Gly | Cys | Cys | Ile | Val | Gly | Gln | Ser | Glu | Gln |
| Leu | Val | Pro | Ala | Asp | Gly | Ile | Leu | Tyr | Ala | Ala | Arg | Asp | Val | Thr |
| Ala | Thr | Val | Asp | Ser | Leu | Pro | Leu | Ile | Thr | Ala | Ser | Ile | Leu | Ser |
| Lys | Lys | Leu | Val | Glu | Gly | Leu | Ser | Ala | Leu | Val | Val | Asp | Val | Lys |
| Phe | Gly | Gly | Ala | Ala | Val | Phe | Pro | Asn | Gln | Glu | Gln | Ala | Arg | Glu |

-continued

| | | | | | | | | | | | | | | |
|---|---|---|---|---|---|---|---|---|---|---|---|---|---|---|
| Leu | Ala | Lys | Thr | Leu | Val | Gly | Val | Gly | Ala | Ser | Leu | Gly | Leu | Arg |
| Val | Ala | Ala | Ala | Leu | Thr | Ala | Met | Asp | Lys | Pro | Leu | Gly | Arg | Cys |
| Val | Gly | His | Ala | Leu | Glu | Val | Glu | Glu | Ala | Leu | Leu | Cys | Met | Asp |
| Gly | Ala | Gly | Pro | Pro | Asp | Leu | Arg | Asp | Leu | Val | Thr | Thr | Leu | Gly |
| Gly | Ala | Leu | Leu | Trp | Leu | Ser | Gly | His | Ala | Gly | Thr | Gln | Ala | Gln |
| Gly | Ala | Ala | Arg | Val | Ala | Ala | Ala | Leu | Asp | Asp | Gly | Ser | Ala | Leu |
| Gly | Arg | Phe | Glu | Arg | Met | Leu | Ala | Ala | Gln | Gly | Val | Asp | Pro | Gly |
| Leu | Ala | Arg | Ala | Leu | Cys | Ser | Gly | Ser | Pro | Ala | Glu | Arg | Arg | Gln |
| Leu | Leu | Pro | Arg | Ala | Arg | Glu | Gln | Glu | Glu | Leu | Leu | Ala | Pro | Ala |
| Asp | Gly | Thr | Val | Glu | Leu | Val | Arg | Ala | Leu | Pro | Leu | Ala | Leu | Val |
| Leu | His | Glu | Leu | Gly | Ala | Gly | Arg | Ser | Arg | Ala | Gly | Glu | Pro | Leu |
| Arg | Leu | Gly | Val | Gly | Ala | Glu | Leu | Leu | Val | Asp | Val | Gly | Gln | Arg |
| Leu | Arg | Arg | Gly | Thr | Pro | Trp | Leu | Arg | Val | His | Arg | Asp | Gly | Pro |
| Ala | Leu | Ser | Gly | Pro | Gln | Ser | Arg | Ala | Leu | Gln | Glu | Ala | Leu | Val |
| Leu | Ser | Asp | Arg | Ala | Pro | Phe | Ala | Ala | Pro | Leu | Pro | Phe | Ala | Glu |
| Leu | Val | Leu | Pro | Pro | Gln | Gln | | | | | | | | |

11. The transformed host cell of claim 7, wherein said replicable expression vector encodes platelet derived endothelial cell growth factor having amino acid sequence:

| | | | | | | | | | | | | | | |
|---|---|---|---|---|---|---|---|---|---|---|---|---|---|---|
| | | | | | Met | Ala | Ala | Leu | Met | Thr | Pro | Gly | Thr | Gly |
| Ala | Pro | Pro | Ala | Pro | Gly | Asp | Phe | Ser | Gly | Glu | Gly | Ser | Gln | Gly |
| Leu | Pro | Asp | Pro | Ser | Pro | Glu | Pro | Lys | Gln | Leu | Pro | Glu | Leu | Ile |
| Arg | Met | Lys | Arg | Asp | Gly | Gly | Arg | Leu | Ser | Glu | Ala | Asp | Ile | Arg |
| Gly | Phe | Val | Ala | Ala | Val | Val | Asn | Gly | Ser | Ala | Gln | Gly | Ala | Gln |
| Ile | Gly | Ala | Met | Leu | Met | Ala | Ile | Arg | Leu | Arg | Gly | Met | Asp | Leu |
| Glu | Glu | Thr | Ser | Val | Leu | Thr | Gln | Ala | Leu | Ala | Gln | Ser | Gly | Gln |
| Gln | Leu | Glu | Trp | Pro | Glu | Ala | Trp | Arg | Gln | Gln | Leu | Val | Asp | Lys |
| His | Ser | Thr | Gly | Gly | Val | Gly | Asp | Lys | Val | Ser | Leu | Val | Leu | Ala |
| Pro | Ala | Leu | Ala | Ala | Cys | Gly | Cys | Lys | Val | Pro | Met | Ile | Ser | Gly |
| Arg | Gly | Leu | Gly | His | Thr | Gly | Gly | Thr | Leu | Asp | Lys | Leu | Glu | Ser |
| Ile | Pro | Gly | Phe | Asn | Val | Ile | Gln | Ser | Pro | Glu | Gln | Met | Gln | Val |
| Leu | Leu | Asp | Gln | Ala | Gly | Cys | Cys | Ile | Val | Gly | Gln | Ser | Glu | Gln |
| Leu | Val | Pro | Ala | Asp | Gly | Ile | Leu | Tyr | Ala | Ala | Arg | Asp | Val | Thr |
| Ala | Thr | Val | Asp | Ser | Leu | Pro | Leu | Ile | Thr | Ala | Ser | Ile | Leu | Ser |
| Lys | Lys | Leu | Val | Glu | Gly | Leu | Ser | Ala | Leu | Val | Val | Asp | Val | Lys |
| Phe | Gly | Gly | Ala | Ala | Val | Phe | Pro | Asn | Gln | Glu | Gln | Ala | Arg | Glu |
| Leu | Ala | Lys | Thr | Leu | Val | Gly | Val | Gly | Ala | Ser | Leu | Gly | Leu | Arg |
| Val | Ala | Ala | Ala | Leu | Thr | Ala | Met | Asp | Lys | Pro | Leu | Gly | Arg | Cys |
| Val | Gly | His | Ala | Leu | Glu | Val | Glu | Glu | Ala | Leu | Leu | Cys | Met | Asp |
| Gly | Ala | Gly | Pro | Pro | Asp | Leu | Arg | Asp | Leu | Val | Thr | Thr | Leu | Gly |
| Gly | Ala | Leu | Leu | Trp | Leu | Ser | Gly | His | Ala | Gly | Thr | Gln | Ala | Gln |
| Gly | Ala | Ala | Arg | Val | Ala | Ala | Ala | Leu | Asp | Asp | Gly | Ser | Ala | Leu |
| Gly | Arg | Phe | Glu | Arg | Met | Leu | Ala | Ala | Gln | Gly | Val | Asp | Pro | Gly |
| Leu | Ala | Arg | Ala | Leu | Cys | Ser | Gly | Ser | Pro | Ala | Glu | Arg | Arg | Gln |
| Leu | Leu | Pro | Arg | Ala | Arg | Glu | Gln | Glu | Glu | Leu | Leu | Ala | Pro | Ala |
| Asp | Gly | Thr | Val | Glu | Leu | Val | Arg | Ala | Leu | Pro | Leu | Ala | Leu | Val |
| Leu | His | Glu | Leu | Gly | Ala | Gly | Arg | Ser | Arg | Ala | Gly | Glu | Pro | Leu |
| Arg | Leu | Gly | Val | Gly | Ala | Glu | Leu | Leu | Val | Asp | Val | Gly | Gln | Arg |
| Leu | Arg | Arg | Gly | Thr | Pro | Trp | Leu | Arg | Val | His | Arg | Asp | Gly | Pro |
| Ala | Leu | Ser | Gly | Pro | Gln | Ser | Arg | Ala | Leu | Gln | Glu | Ala | Leu | Val |
| Leu | Ser | Asp | Arg | Ala | Pro | Phe | Ala | Ala | Pro | Leu | Pro | Phe | Ala | Glu |
| Leu | Val | Leu | Pro | Pro | Gln | Gln | | | | | | | | |

* * * * *

UNITED STATES PATENT AND TRADEMARK OFFICE
CERTIFICATE OF CORRECTION

PATENT NO. : 5,227,302                                   Page 1 of 2

DATED       : July 13, 1993

INVENTOR(S) : Carl Henrik-Heldin et al.

It is certified that error appears in the above-identified patent and that said Letters Patent is hereby corrected as shown below:

Column 5, line 3:   change "Wlkman" to -- Folksman --.

Column 5, line 50:  change "sane" to -- same --.

Column 6, line 32:  change "chrmoatographic" to -- chromatographic --.

Column 7, line 45:  change "DP-ECGF" to -- PD-ECGF --.

Column 8, line 3:   change "261 1616-1625" to -- 26: 1617-1625 --.

Column 8, line 67:  change "Humabn" to -- human --.

Column 9, line 16:  change "Molone" to -- Moloney --.

Column 10, line 7:  change "Molone" to -- Moloney --.

Column 11, line 61: change "would" to -- wound --.

Column 12, line 12: change "et al 1987" to -- et al, supra --.

Column 18, line 41: change "grwoth" to -- growth --.

Column 21, line 49: change "gestatum" to -- gestation --.

UNITED STATES PATENT AND TRADEMARK OFFICE
CERTIFICATE OF CORRECTION

PATENT NO. : 5,227,302

DATED : July 13, 1993

INVENTOR(S) : Carl Henrik-Heldin et al

It is certified that error appears in the above-indentified patent and that said Letters Patent is hereby corrected as shown below:

Column 24, line 47: change "Molone" to -- Moloney --.

Signed and Sealed this

Eleventh Day of April, 1995

Attest:

BRUCE LEHMAN

Attesting Officer

Commissioner of Patents and Trademarks